(12) United States Patent
Peltz et al.

(10) Patent No.: US 9,226,918 B2
(45) Date of Patent: Jan. 5, 2016

(54) METHODS AND COMPOSITIONS FOR TREATING OR PREVENTING NARCOTIC WITHDRAWAL SYMPTOMS

(75) Inventors: Gary Peltz, Redwood City, CA (US); David Clark, Palo Alto, CA (US); Lawrence Chu, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1243 days.

(21) Appl. No.: 12/631,628

(22) Filed: Dec. 4, 2009

(65) Prior Publication Data

US 2010/0144754 A1 Jun. 10, 2010

Related U.S. Application Data

(60) Provisional application No. 61/120,003, filed on Dec. 4, 2008.

(51) Int. Cl.
| | | |
|---|---|---|
| *A61K 31/485* | (2006.01) | |
| *A61K 31/4178* | (2006.01) | |
| *A61K 31/444* | (2006.01) | |
| *A61K 31/495* | (2006.01) | |

(52) U.S. Cl.
CPC ........... *A61K 31/4178* (2013.01); *A61K 31/444* (2013.01); *A61K 31/485* (2013.01); *A61K 31/495* (2013.01)

(58) Field of Classification Search
None
See application file for complete search history.

(56) References Cited

U.S. PATENT DOCUMENTS

| | | | | | |
|---|---|---|---|---|---|
| 4,847,281 | A | * | 7/1989 | Tyers | 514/397 |
| 5,057,519 | A | * | 10/1991 | Suberg | 514/282 |
| 6,103,734 | A | * | 8/2000 | Legarda Ibanez | 514/282 |
| 6,630,612 | B2 | | 10/2003 | Allan et al. | |
| 2004/0146469 | A1 | * | 7/2004 | Reed et al. | 424/59 |
| 2006/0293309 | A1 | | 12/2006 | Thor et al. | |
| 2007/0072899 | A1 | | 3/2007 | Johnson et al. | |
| 2008/0004260 | A1 | | 1/2008 | Singh | |
| 2008/0004291 | A1 | | 1/2008 | Singh | |
| 2009/0175939 | A1 | | 7/2009 | Bosse et al. | |

FOREIGN PATENT DOCUMENTS

| | | |
|---|---|---|
| WO | 8803801 A1 | 6/1988 |
| WO | 03086361 A1 | 10/2003 |
| WO | 2008005345 A2 | 1/2008 |
| WO | 2008005345 A3 | 1/2008 |
| WO | 2008077092 A2 | 6/2008 |
| WO | 2008077092 A3 | 6/2008 |
| WO | 2008070268 A2 | 10/2008 |
| WO | 2008128126 A1 | 10/2008 |

OTHER PUBLICATIONS

"Ondansetron, Orally Disintegrating Tablets Versus Intravenous Injection for Prevention of Intrathecal Morphine-Induced Nausea, Vomiting, and Pruritus in Young Males" by Pirat et al., Anesth. Analg. 101, 1330-36 (2005).*
"The pharmacokinetics of ondansetron after intravenous injection in healthy volunteers phenotyped as poor or extensive metabolisers of debrisoquine" by Ashforth et al., Br. J. Clin. Pharmac. 37, 389-91 (1994).*
"Three patients and their drugs: A parallel case paper on paediatric opiate use and withdrawal" by Siden et al., Paediatr. Child Health 10, 163-68 (2005).*
"Suppression of histamine-induced pruritis by three antihistamine drugs" by Rhoads et al., J. Allergy Clin. Immunol. 55, 180-05 (1975) (PubMed Abatract 234488).*
"Two new rating scales for opiate withdrawal" by Handelsman et al., Am. J. Drug Alcohol Abuse 13, 293-380 (1987).*
"Methadone" by Kim, Can. Med. Assoc. J. 109, 615-19 (1973).*
"Narcotic withdrawal syndrome after intrathecal administration of morphine" by Messahel et al., Br. Med. J. 283, 471-72 (1981).*
"Reduction of opioid-withdrawal symptoms with quetiapine" by Pinkofsky et al., J. Clin. Psychiatry 66, 1285-58 (2005).*
"Ondansetron and opiate craving. A novel pharmacological approach to addiction" by Sell et al. Br. J. Psychiatry 166, 511-14 (1995).*
Acquas, et al., "5-HT3 receptors antagonists block morphine- and nicotine- but not amphetamine-induced place-preference conditioning," Pharmacological Research Commununications, Dec. 1988, vol. 20, No. 12, 1113-1114.
Carboni, et al., "5-HT3 receptor antagonists block morphine- and nicotine-induced place-preference conditioning," European Journal of Pharmacology, 1988, No. 151, 159-60.
Higgins, et al., "Effect of the 5-HT3 receptor antagonists, MDL72222 and ondansetron on morphine place conditioning," Psychopharmacology, 1992, 106:315-20.
Joharchi, et al., "Effect of 5-HT3 receptor antagonists on the discriminative stimulus properties of morphine in rats," Psychopharmacology, 1993, 112:111-115.
Borg, et al., "Voluntary Oral Morphine Self-Administration in Rats: Effect of Haloperidol or Ondansetron," Pharmacololgy Biochemistry and Behavior, 1994, vol. 47, No. 3, 633-646.
Higgins, et al., "Influence of 5-HT3 receptor antagonists and the indirect 5-HT agonist, dexfenfluramine, on heroin self-administration in rats," Psychopharmacology, 1994, 114:611-619.
Sell, et al., "Ondansetron and Opiate Craving. A Novel Pharmacological Approach to Addiction," British Journal of Psychiatry, 1995, No. 166, 511-514.
Hui, et al., "Prevention by the 5-HT3 receptor antagonist, ondansetron, of morphine-dependence and tolerance in the rat," British Journal of Pharmacology, 1996, 118, 1044-1050.

(Continued)

*Primary Examiner* — Theodore R West
(74) *Attorney, Agent, or Firm* — David J. Aston; Bozicevic, Field & Francis LLP

(57) ABSTRACT

This invention provides methods and pharmaceutical compositions for preventing or treating physical dependence and/or withdrawal associated with narcotic use, in particular by modulating a 5-HT3 receptor. Using a computational genetic approach in mice, a gene conserved between mice and humans was identified as candidate as a modulator of physical dependence to morphine. Administration of compounds that modulate 5-HT3 receptors was found to control withdrawal from morphine in mice and humans.

2 Claims, 11 Drawing Sheets

(56) References Cited

OTHER PUBLICATIONS

Pinelli, et al., "Effects of ondansetron administration on opioid withdrawal syndrome observed in rats," European Journal of Pharmacology, 1997, 340, 111-119.

O'Brien, et al., "A comparison of papaveretum-promethazine with morphine-ondansetron for patient-controlled analgesia," Ir J Med Sci., 2000, 169:58-59.

Crews, et al.,"Lack of effect of ondansetron on the pharmacokinetics and analgesic effects of morphine and metabolites after single-dose morphine administration in healthy volunteers," British Journal of Clinical Pharmacology, Jan. 10, 2001, 51, 309-316.

Hodge, et al., "5-HT3A Receptor Subunit is Required for 5-HT3 Antagonist-Induced Reductions in Alcohol Drinking," Neuropsychopharmacology, 2004, 29, 1807-1813.

Guo, et al., "Understanding Our Drugs and Our Diseases," Proceedings of the American Thoracic Society, 2006, vol. 3, 409-412.

Jellish, et al., "Morphine/ondansetron PCA for postoperative pain, nausea, and vomiting after skull base surgery," Otolaryngology-Head and Neck Surgery, 2006, 135, 175-181.

Mouedden, et al., "Pharmacological evaluation of opioid and non-opioid analgesics in a murine bone cancer model of pain," Pharmacology, Biochemistry and Behavior, 2007, 86, 458-467.

Boonmak, et al., "Antiemetic effect of ondansetron 0.2 mg mL-1 in PCA morphine solution," European Journal of Anaesthesiology, 2007, 24:664-667.

Chu, et al., "From mouse to man: the 5-HT3 receptor modulates physical dependence on opioid narcotics," Pharmacogenetics and Genomics, 2009, 19:193-205.

Niesler, et al., "Serotonin type 3 receptor genes: HTR3A, B, C, D, E," Pharmacogenomics, 2008, vol. 9, No. 5, 501-504.

Hain, T. C., "Treatment of Emesis (Vomiting)," Available at http://www.dizziness-and-balance.com/treatment/drug/emesis.html. Accessed Jan. 7, 2010.

International Narcotics Control Board. List of Narcotic Drugs Under International Control. Protocol of Mar. 25, 1972 amending the convention on Narcotic Drugs, 1961. Available at http://www.incb.org/pdf/e/list/46thedition.pdf. Accessed Jan. 7, 2010.

PCT International Search Report PCT/US09/66877, Feb. 25, 2010.

CN Office Action, Application No. 200980156104.9, Mar. 29, 2013, 4 pp.

\* cited by examiner

A

B

METHODS AND COMPOSITIONS FOR TREATING OR PREVENTING NARCOTIC WITHDRAWAL SYMPTOMS

CROSS-REFERENCE

This application claims the benefit of U.S. Patent Application Ser. No. 61/120,003 filed on Dec. 4, 2008, which is incorporated herein by reference in its entirety.

FEDERALLY-SPONSORED RESEARCH OR DEVELOPMENT

This invention was made with Government support under contracts GM071400 and DA021332 awarded by the National Institutes of Health. The Government has certain rights in this invention.

BACKGROUND OF THE INVENTION

Addiction to illicit and prescription opioid narcotic drugs (heroin, morphine, codeine, oxycodone and related agents) is a significant public health issue. Each month in the US, 4.9% of persons aged 12 or older (>11 million) use prescription pain relievers for non-medical purposes. Young adults (age 18 to 25) are particularly hard hit by this problem, and they have the highest rate of abuse of prescription pain relievers (Results from the 2006 National Survey on Drug Use and Health: National Findings. Substance Abuse and Mental Health Services Administration, Department of Health and Human Services, 2006). Opioid addiction has adverse consequences for personal health and society (Birnbaum, H. G., et al., *Clin J Pain*, 2006. 22(8): p. 667-676; Gruber, S. A. et al. *Neuropsychol Rev*, 2007. 17(3): p. 299-315; Manchikanti, L., *Pain Physician*, 2006. 9(4): p. 287-321). As many as 90% of patients in chronic pain management settings receive opioid pain relievers, and the prevalence of drug abuse is 9-41% among these patients (Manchikanti, L., supra). Anxiety, increased pain sensitivity, poor concentration, tachycardia and flu-like symptoms develop during opioid withdrawal, a syndrome reflecting physical dependence on these drugs (Handelsman, L., et al., *Am J Drug Alcohol Abuse*, 1987. 13(3): p. 293-308). The severity of the dependence and resulting withdrawal symptoms is a major contributor to the addictive potential of opioid narcotics. Current strategies for treatment of opioid withdrawal are suboptimal; they rely on the administration of controlled substances (methadone and buprenorphine), or medications with significant hemodynamic side effects (clonidine).

The misuse of and addiction to opioid drugs can be initiated after exposure to prescribed medications in a clinic (or involve a medical source). Thus, clinical interventions that reduce the risk for misuse and addiction could have a substantial impact on this public health problem. A prevention model has not been previously pursued in which physicians co-prescribe medications in combination with addicting agents to reduce the risk of subsequent misuse, dependence, or addiction. This is due to most of the addicting agents (cocaine, heroin, marijuana) were illicit drugs obtained from non medical sources. However, opioid narcotics are commonly obtained from legitimate medical sources. Therefore, this raises the probability that co-administration a medication that alleviates the iatrogenic influences that contribute to and sustain the misuse and abuse of prescription opiate medications would be of substantial benefit.

Since it could lead to new approaches for prevention or treatment of addiction, identification of novel genetic factors affecting dependence on opioids is also of great public health significance. Susceptibility to opioid addiction is heritable in humans (Kendler, K. S., et al. *Am J Psychiatry*, 2003. 160(4): p. 687-695). One dimension of addiction is physical dependence which can be modeled in rodents. The jumping behavior displayed by morphine-dependent mice after administration of naloxone, a potent opioid receptor antagonist, is a commonly used measure of physical dependence. Naloxone-precipitated jumping is a highly heritable trait amongst inbred mouse strains (Kest, B., et al., *Mamm Genome*, 2004. 15(8): p. 610-617), and the inter-strain differences are largely independent of differences in the method of drug administration or the duration of treatment (Kest, B., et al. *Pharmacol Biochem Behav* 2002. 73(4): p. 821-828; Liang, D. Y., et al. *Pain*, 2006. 121(3): p. 232-240). Furthermore, naloxone-precipitated withdrawal has been used to quantify opioid dependence in human volunteers (Bickel, W. K., et al., *NIDA Res Monogr*, 1986. 67: p. 349-54). Despite these facts, no specific genes linked to physical dependence have been identified.

Computational genetic mapping (Wang, J., et al., *Trends Genet*. 2005. 21(9): p. 526-532; Liao, G., et al., *Science*, 2004. 306(5696): p. 690-695) can be used to identify several genetic factors underlying the variability in morphine-induced alterations in pain sensitivity (hyperalgesia) and responsiveness to analgesic medications in mice (Liang, D. Y., et al., *Pharmacogenet Genomics* 2006. 16(11): p. 825-835; Liang, D. Y., et al. *Anesthesiology*, 2006. 104(5): p. 1054-1062; Smith, S. B., et al., *Pharmacogenet Genomics*, 2008. 18(3): p. 231-241). Haplotype-based computational genetic mapping can be used to identify genes affecting susceptibility to opioid dependence in mice, and a pharmacologic agent targeting the human homologue of the computationally identified murine gene can alleviate the signs and symptoms of withdrawal in humans.

SUMMARY OF THE INVENTION

The following brief summary is not intended to include all features and aspects of the present invention, nor does it imply that the invention must include all features and aspects discussed in this summary.

The present invention comprises, in certain aspects, a method for preventing or treating physical dependence and/or withdrawal symptoms associated with narcotic use in a subject, comprising administering to said subject an agent that modulates a 5-HT3 receptor. In certain aspects, a method for preventing or treating physical dependence and/or withdrawal symptoms associated with narcotic use in a subject is provided, consisting of administering to said subject an agent that modulates a 5-HT3 receptor. In certain aspects, a method for preventing or treating physical dependence and/or withdrawal symptoms associated with narcotic use in a subject is provided, consisting essentially of administering to said subject an agent that modulates a 5-HT3 receptor. The subject may be a human subject, and in certain embodiments, the narcotic may be, or comprise, morphine. In certain aspects of the invention, the agent is a 5-HT3 receptor antagonist, which may in certain instances be ondansetron or palonosetron.

In certain aspects of the invention, the agent is administered to said subject before administration of an opioid antagonist to said subject. In certain aspects of the invention, the agent may also be administered to said subject before or after administration of said narcotic to said subject. Also, in certain aspects of the invention, the agent may be co-administered with said narcotic to said subject. In certain aspects of the invention, the agent is up to 16 mg of ondansetron or up to 1.5 mg palonosetron.

In certain aspects of the invention, there are provided methods for preventing or treating physical dependence and/or withdrawal symptoms associated with narcotic use in a subject comprising administering to the subject a pharmaceutical composition comprising a narcotic and an agent that reduces physical dependence and/or withdrawal symptoms associated with use of said narcotic. In certain aspects of the invention, there are provided methods for preventing or treating physical dependence and/or withdrawal symptoms associated with narcotic use in a subject comprising administering to the subject a pharmaceutical composition consisting of a narcotic and an agent that reduces physical dependence and/or withdrawal symptoms associated with use of said narcotic. In certain aspects of the invention, there are provided methods for preventing or treating physical dependence and/or withdrawal symptoms associated with narcotic use in a subject comprising administering to the subject a pharmaceutical composition consisting essentially of a narcotic and an agent that reduces physical dependence and/or withdrawal symptoms associated with use of said narcotic. In certain aspects of the invention, the subject is a human. In certain aspects of the invention, said narcotic is or comprises morphine. In certain aspects of the invention, the agent modulates a 5-HT3 receptor. In certain aspects of the invention, the agent is a 5-HT3 receptor antagonist. In certain aspects of the invention, the agent is ondansetron or palonosetron. In certain aspects of the invention, the narcotic is up to 16 mg morphine and the agent is up to 16 mg ondansetron or up to 1.5 mg palonosetron.

In certain aspects of the invention, there is provided a method for treating addiction to a narcotic in a subject comprising administering to said subject an agent that modulates a 5-HT3 receptor. Here again, in certain aspects of the invention, the subject is a human. In certain aspects of the invention, the narcotic is morphine. In certain aspects of the invention, the agent is a 5-HT3 receptor antagonist. In certain aspects of the invention, the agent is ondansetron or palonosetron.

In certain aspects of the invention, there is provided pharmaceutical compositions comprising a narcotic and an agent that reduces physical dependence and/or withdrawal symptoms associated with use of said narcotic. In certain aspects of the invention there are provided pharmaceutical compositions consisting of a narcotic and an agent that reduces physical dependence and/or withdrawal symptoms associated with use of said narcotic. In certain aspects of the invention, there are provided pharmaceutical compositions consisting essentially of a narcotic and an agent that reduces physical dependence and/or withdrawal symptoms associated with use of said narcotic. In certain aspects of the invention, the narcotic is or comprises morphine. In certain aspects of the invention, the agent modulates a 5-HT3 receptor. In certain aspects of the invention, the agent is a 5-HT3 antagonist. In certain aspects of the invention, the agent is ondansetron or palonosetron.

In certain aspects of the invention, there is provided methods of treating or preventing physical dependence and/or withdrawal symptoms associated with narcotic use in a subject comprising administering to said subject an agent that modulates a 5-HT3 receptor and a second agent. In certain aspects of the invention, there is provided methods for treating or preventing physical dependence and/or withdrawal symptoms associated with narcotic use in a subject consisting of administering to said subject an agent that modulates a 5-HT3 receptor and a second agent. In certain aspects of the invention, there is provided methods for treating or preventing physical dependence and/or withdrawal symptoms associated with narcotic use in a subject consisting essentially of administering to said subject an agent that modulates a 5-HT3 receptor and a second agent. Again, in certain aspects of the invention, the subject is a human. In certain aspects of the invention, the narcotic is morphine. In certain aspects of the invention, the agent is a 5-HT3 receptor antagonist. In certain aspects of the invention, the agent is ondansetron or palonosetron. In certain aspects of the invention, the second agent is an antiemetic agent. In certain aspects of the invention, said antiemetic agent is an antihistamine. In certain aspects of the invention, said antihistamine is hydroxyzine. In certain aspects of the invention, the agent that modulates a 5-HT3 receptor and the second agent are administered before the narcotic is administered to the subject. In certain aspects of the invention, the agent that modulates a 5-HT3 receptor and said second agent are administered after the narcotic is administered to the subject. In certain aspects of the invention, the agent that modulates a 5-HT3 receptor and the second agent are co-administered with the narcotic to the subject.

In certain aspects of the invention, there are provided pharmaceutical compositions comprising a narcotic and at least two agents that reduce physical dependence and/or withdrawal symptoms associated with use of said narcotic. In certain aspects of the invention, two agents comprise a 5-HT3 receptor modulator and a second agent. In certain aspects of the invention, said 5-HT3 receptor modulator is a 5-HT3 antagonist. In certain aspects of the invention, the second agent is an antihistamine. In certain aspects of the invention, the 5-HT3 receptor modulator is ondansetron or palonosetron and said second agent is hydroxyzine. In certain aspects of the invention, the narcotic is morphine. In certain aspects of the invention, the narcotic is morphine, the 5-HT3 receptor modulator is ondansetron or palonosetron, and another agent is hydroxyzine. In certain aspects of the invention, the narcotic is up to 20 mg morphine, said 5-HT3 receptor modulator is up to 1.5 mg palonosetron, and the other agent is up to 200 mg hydroxyzine.

In certain aspects of the invention, there are provided pharmaceutical compositions consisting of a narcotic and two agents that reduce physical dependence and/or withdrawal symptoms associated with use of said narcotic. In certain aspects of the invention, there are provided pharmaceutical composition consisting essentially of a narcotic and two agents that reduce physical dependence and/or withdrawal symptoms associated with use of said narcotic. In certain aspects of the invention, one agent is an agent that modulates a 5-HT3 receptor. In certain aspects of the invention, one agent is an antiemetic. In certain aspects of the invention, both agents are antiemetics. In certain aspects of the invention, one agent is an antihistamine. In certain aspects of the invention, the narcotic is morphine. In certain aspects of the invention, one agent is a 5-HT3 receptor antagonist and the other agent is an antihistamine. In certain aspects of the invention, one agent is ondansetron or palonosetron, and the other agent is hydroxyzine. In certain aspects of the invention, the narcotic is morphine, one agent is ondansetron or palonosetron, and the other agent is hydroxyzine. In certain aspects of the invention, the narcotic is up to 20 mg morphine, one agent is up to 1.5 mg palonosetron, and the other agent is up to 200 mg hydroxyzine.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
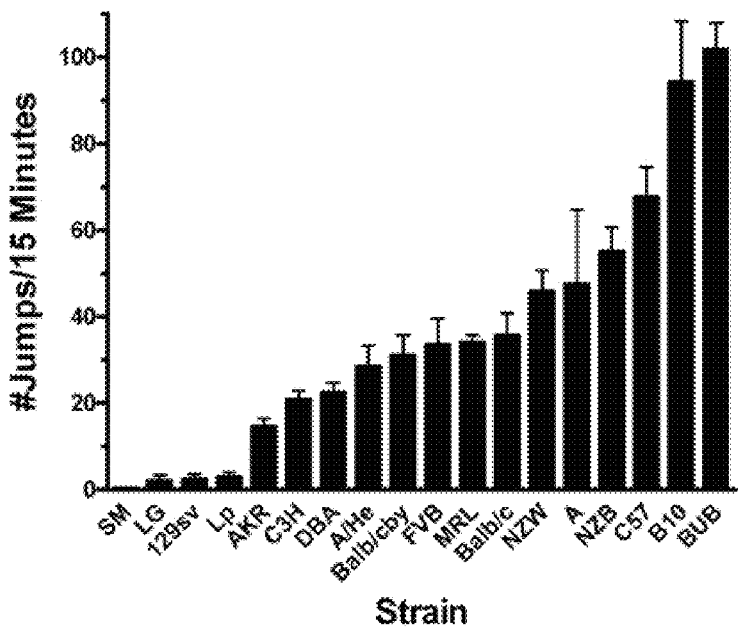
FIG. 1 illustrates inter-strain differences in physical dependence on morphine and computational genetic analysis of the inter-strain differences.

The present invention provides methods and compositions for reducing, preventing, or treating physical dependence and/or withdrawal symptoms associated with narcotic use. In another aspect, the present invention provides methods and compositions for preventing or treating addiction to a narcotic. In general, the methods and compositions for reducing, preventing, treating physical dependence and/or withdrawal symptoms associated with narcotic use are directed toward modulating 5-HT3 receptors. 5-HT3 receptors are involved in controlling narcotic withdrawal in humans. In one embodiment, the methods for treatment of physical dependence and/or withdrawal symptoms associated with narcotic use target 5-HT3 receptors.

The methods of the invention include identification of genes that can modulate the physical dependence and/or withdrawal symptoms associated with narcotic use. Also described herein are methods of treatment of the physical dependence and/or withdrawal symptoms associated with narcotic use.

I. Haplotype-Based Computational Genetic Mapping

Haplotype-based computational genetic mapping enables the identification a causative genetic factor by correlating a pattern of observable physiologic or pathologic differences among selected inbred strains with a pattern of genetic variation. Genomic regions where the pattern of genetic variation has the strongest correlation with the trait distribution among the inbred strains analyzed are then identified. Depending on the type of trait analyzed, the phenotypic data can be obtained within a day to a week after starting the experiment. Once the phenotypic data are obtained, the data can be computationally analyzed and the predictions evaluated by a single scientist within a single day.

For computational mapping, the pattern of genetic variation was characterized by identifying single nucleotide polymorphisms (SNPs) within a genomic region and determining the alleles at each SNP position for 18 inbred strains of mice analyzed. The extent of linkage disequilibrium among SNP alleles within a region was calculated, and a map of haplotype blocks within genomic regions with high linkage disequilibrium was produced. The SNPs and haplotype map of the inbred strain genome are displayed at http://mouseSNP.roche.com. The computational mapping program assesses the extent of correlation between the trait values and strain groupings within each haplotype block using analysis of variance-based statistical modeling. To assess this correlation, a p value is calculated to determine if the data are consistent with the null hypothesis that the mean trait values for inbred strains with the same genotypic haplotype are equal.

Haplotype-based computational genetic mapping was used to identify genes affecting susceptibility to opioid dependence in mice. One of the genes is HTR3A, which encodes a component of the 5-HT3 receptor.

II. Physical Dependence and Withdrawal Associated with Narcotic Use

The methods and compositions of the present invention relate to physical dependence and/or withdrawal symptoms or addiction associated with narcotic use. Narcotics can travel through the bloodstream to the brain where they can bind to mu opioid receptors on the surfaces of opiate-sensitive neurons. Binding of narcotics to receptors can result in feelings of pleasure. Narcotics are often administered to relieve pain; however, when the reward processes are activated in the absence of pain, repeated use of the narcotic for pleasure can result. The narcotic can be administered to a narcotic user by a variety of routes, including, for example, oral, transdermal (e.g., skin patches), intravenous, or as suppositories; in addition, the drugs can be administered by smoking or snorting. The narcotic can be administered in a medical setting, for example, a clinic or a hospital, etc.

Addiction can result from elevated narcotic use that becomes compulsive and self-destructive. Narcotic addiction can be characterized by continued use of a drug despite acknowledged harm from the drug, excessive preoccupation with use of the drug, and social isolation. Repeated exposure to increasing dosages of narcotics can alter the brain so that it functions normally when the drugs are present and abnormally when they are not. This alteration can result in tolerance (need to take increasing dosages of the narcotic to achieve the same opioid effect) and dependence, or the susceptibility to withdrawal symptoms. Symptoms of narcotic withdrawal can follow cessation or reduction in use of a narcotic that has been heavy or prolonged (over several weeks or longer), or after administration of an opioid antagonist after a period of opioid use.

Opioid dependence and opioid withdrawal symptoms can arise from changes in the locus ceruleus (LC). Neurons in the LC produce a chemical, noradrenaline (NA) and distribute it to parts of the brain where it stimulates general alertness, among other functions. When opioid molecules link to mu receptors on the brain cells in the LC, the neuron's release of NA is suppressed, which can result in drowsiness, slowed respiration, and low blood pressure. Repeated exposure to opioids, however, can result in the LC neurons increasing their level of activity. When opioids are present, their suppressive impact is offset by the heightened activity, and the normal amounts of NA make the patient feel more or less normal. When opioids are not present to suppress the LC brain cells' heightened activity, the neurons release excessive amounts of NA, which can trigger anxiety, muscle cramps, and diarrhea. Other brain areas can also contribute to the production of withdrawal symptoms, including the mesolimbic reward system.

Symptoms of narcotic withdrawal can include diarrhea, dysphoric mood, fever, insomnia (chronic), lacrimation (producing tears) or rhinorrhea (running nose), muscle aches, nausea or vomiting, pupillary dilation (mydriasis), piloerection (goosebumps), sweating, tachycardia, flu-like symptoms, tremor, abdominal cramps, restlessness, shivering, muscle twitches, hot/cold flushes, increased respiratory rate (rapid breathing), salivation, lack of appetite and yawning. Mental symptoms can include depression, anxiety, panic, irritability, poor concentration, confusion, and craving for the narcotic.

The methods and pharmaceutical compositions of the present invention can be used to treat physical dependence and/or withdrawal symptoms associated with use of a narcotic by a subject. The subject can be any mammal who has used or is currently using a narcotic. The subject can be a rat, mouse, or a human. The subject may or may not be addicted to the narcotic. The methods and pharmaceutical compositions of the present invention can be used to treat narcotic addiction.

A. Narcotics

The methods and pharmaceutical compositions of the present invention for reducing, preventing, or treating physical dependence and/or withdrawal symptoms, or preventing or treating addiction, associated with narcotic use. Narcotics can include, for example: acetorphine, acetyl-alpha-methylfentanyl, acetylmethadol, alfentanil, allylprodine, alphacetylmethadol, alphameprodine, alphmethadol, alpha-methylfentayl, alpha-methylthiofentanyl, alphaprodine, anileridine, benzethidine, benzylmorphine, betacetylmethadol, beta-hydroxyfentanyl, beta-hydroxy-3-methylfentanyl, betameprodine, betamthadol, betaprodine, bezitramide, cannabis and cannabis resin and extracts and tinctures of cannabis, clonitazene, coca leaf, cocaine, codoxime, concentrate of poppy straw, desomorphine, dextromoramide, diampromide, diethylthiambutene, difenoxin, dihydroetorphine, dihydromorphine, dimenoxadol, dimepheptanol, dimethylthiambutene, dioxaphetyl butyrate, diphenoxylate, dipipanone, drotebanol, ecgonine, ethylmethylthiambutene, etonitazene, etorphine, etoxeridine, fentanyl, furethidine, heroin, hydrocodone, hydromorphinol, hydromorphone, hydroxypethidine, isomethadone, ketobemidone, levomethorphan, levomoramide, levophenacylmorphan, levorphanol, metazocine, methadone, methadone intermediate, methyldesorphine, methyldihydromorphine, 3-methylfentanyl, 3-methylthiofentanyl, metopon, moramide intermediate, morpheridine, morphine, morphine methobromide, and morphine-N-oxide, MPPP, myrophine, nicomorphine, noracymethadol, norlevorphanol, normethadone, normophine, norpipanone, opium, oxycodone, oxymorphone, para-fluorofentanyl, PEPAO, pethidine, pethidine intermediate A, pethidine intermediate B, pethidine intermediate C, phenadoxone, phenampromide, phenazocine, phenomorphan, phenoperidine, piminodine, piritramide, proheptazine, properidine, racemethorphan, racemoramide, racemorphan, remifentanil, sufentanil, thebacon, thebaine, thiofentanyl, tilidine, and trimeperidiene.

In one embodiment of the present invention, one or more agents that reduce, prevent, or treat physical dependence and/or withdrawal symptoms associated with narcotic use can be co-administered with one or more narcotics to a subject to prevent or treat physical dependence and/or withdrawal symptoms associated with narcotic use. In another embodiment, one or more agents that reduce, prevent, or treat physical dependent and/or withdrawal symptoms associated with narcotic use are administered to a subject before one or more narcotics are administered to the subject. In another embodiment, one or more agents that reduce, prevent, or treat physical dependent and/or withdrawal symptoms associated with narcotic use are administered to a subject after one or more narcotics are administered to the subject. One or more agents that reduce physical dependence and/or withdrawal symptoms associated with narcotic use can be in the same pharmaceutical composition with one or more narcotics that are administered to a subject.

B. Opioid Receptors

Narcotics can bind opioid receptors, which are G-protein coupled receptors (GPCRs) that interact with ligands classified as opioids. There are three main types of opioid receptors: delta ($\delta$), kappa ($\kappa$), and mu ($\mu$). There are two types of delta receptor ($\delta_1$, $\delta_2$) and the delta receptor is found in the brain in pontine nuclei, amygdala, olfactory bulbs, and deep cortex. The delta receptor functions in analgesia, physical dependence, and antidepressant effects. The kappa receptor has three subtypes ($\kappa_1$, $\kappa_2$, and $\kappa_3$) and is found in the brain, including in the claustrum, hypothalamus, and periaqueductal gray, and in the spinal cord, including the substantia gelantinosa. The kappa receptor functions in inhibition of ADH release, miosis, sedation, and spinal analgesia. The mu receptor has three subtypes ($\mu_1$, $\mu_2$, and $\mu_3$) and is located in the brain, including the cortex, thalamus, and periaqueductal gray, and in the spinal cord, including the substantia gelatinosa. The $\mu_1$ receptor is involved in supraspinal analgesia and physical dependence, and the $\mu_2$ receptor is involved in respiratory depression, miosis, euphoria, reduced GI motility, and physical dependence. A fourth opioid receptor family member is the opioid-receptor-like receptor, (ORL1, NOP). The narcotic used by a subject can bind any of the opioid receptors.

The methods and pharmaceutical compositions of the present invention can be directed toward modulating the activity of one or more opioid receptors.

C. Opioid Receptor Antagonists

The methods and pharmaceutical compositions of the present invention can include one or more opioid receptor antagonists. Selective antagonists of opioid receptors that can be suitable for use in the methods and pharmaceutical compositions of the present invention include, for example, CTAP (mu receptor), naltrindole, TIPP-$\psi$, ICI 174864 (delta receptor), nor-binaltorphimine (kappa receptor). Other opioid receptor antagonists suitable for use in methods and pharmaceutical compositions of the present invention include, for example, naloxone, naltrexone, alvimopan, methylnaltrexone (MNTX), nalbuphine, nalorphine, nalmefene, diprenorphine, trans-3,4-dimethyl-4-(3-hydroxyphenyl)piperidine, 5'-acetamidinoethylnaltrindole (ANTI), 4-Aminoquinoline, N-(4-amino-2-methylquinolin-6-yl)-2-(4-ethylphenoxymethyl)benzamide monohydrochloride, 7-Benzylidenenaltrexone, Binaltorphimine; Butorphanol (17-cyclobutylmethyl-3,14-dihydroxymorphinan) tartrate; CTAP, D-Phe-Cys-Tyr-D-Trp-Arg-Thr-Pen-Thr-NH2; CTOP, D-Phe-Cys-Tyr-D-Trp-Orn-Thr-Pen-Thr-NH2 (SEQ ID NO: 32); Cyclazocine; Cyprodime; 1,3-Dimethyl-4-piperidinone; Ethylketocyclazocine; .beta.-Funaltrexamine; GNTI, 5'-Guanidinonaltrindole; ICI 174864, N,N-diallyl-Tyr-Aib-Aib-Phe-Leu (SEQ ID NO: 40); Indolomorphinan; 5'-Isothiocyanate; J-113397, 1-[(3R,4R)-1-Cyclooctylmethyl-3-hydroxymethyl-4-piperidyl]-3-ethyl-1,3-di-hydro-2H-benzimidazol-2-one; JDTic, (3R)-7-Hydroxy-N-[(1S)-1-[[(3R,4R)-4-(3-hydroxyphenyl)-3,4-dimethyl-1-pip-eridinyl]methyl]-2-methylpropyl]-1,2,3,4-tetrahydro-3-isoquinoline-carboxa-mide 3-Quadazocine; Loperamide; Methoxynaltrexone; Mr 2266; Naloxone methiodide; Naloxazone; .beta.-Naltrexamine; Naltriben; Phenylpiperidine; SB-612111, (−)-cis-1-methyl-7-[[4-(2,6-dichlorophenyl)piperidin-1-yl]methyl]-6,7,8,9-tetrahydro-5H-benzocyclohepten-5-ol; SoRI 9409, 59-(4-chlorophenyl)-17-(cyclopropylmethyl)-6,7-didehydro-3,14-dihydroxy-4-, 5a-epoxypyrido-[29, 39:6,7]morphinan, SNC 80; TIPP-y, Tyr-Tic-Phe-Phe; and Triethyleneglycolnaltrexamine.

III. Receptors and Drugs that Regulate Emesis

The methods and compositions of the present invention can target receptor(s) and/or pathway(s) that regulate emesis (vomiting). The vomiting center is found on the lateral medullary reticular formation in the pons, a structure located on the brainstem, and contains receptors and neurotransmitter that regulate emesis. Stimulation of the chemoreceptor trigger zone (CTZ) (area postrema) can lead to vomiting. The CTZ at the fourth ventricle has receptors that play roles in emesis, including 5-HT3 receptors, neurokinin 1 (NK1) receptors, dopamine D2 receptors, opioid receptors, and acetylcholine receptors. The vestibular system also plays roles in emesis. The vestibular system communicates with the brain via cranial nerve VIII (vestibulochochlear nerve), which has muscarinic receptors and H1 histamine receptors. The vomiting center also contains the neurotransmitters choline, histamine, dopamine, serotonin, and opioids.

A. 5-HT3 Receptor

The methods and pharmaceutical compositions of the present invention can target the 5-HT3 receptor. The 5-HT3 (5-hydroxytryptamine-3) receptor is a ligand-gated ion channel. The receptor contains 5 subunits that are positioned around a central ion conducting pore. The subunits are proteins encoded by the genes HTR3A, HTR3B, HTR3C, HTR3D, and/or HTR3E. Functional channels can be comprised of five identical 5-HT3A subunits (homopentameric) or a mixture of 5-HT3A and one of the other four subunits (5-HT3B, 5-HT3C, 5-HT3D, or 5-HT3E; heteropentameric). The pore of the 5-HT3 channel is permeable to sodium, potassium, and calcium ions. The 5-HT3 receptor can bind serotonin (5-hydroxytryptamine, or 5-HT).

5-HT3 receptors are expressed throughout the central and peripheral nervous systems and mediate a variety of physiological functions. The HTR3A, HTR3B, and HTR3C genes are expressed in the CNS and periphery; HTR3D, and HTR3E are expressed in the GI tract. Activation of the 5-HT3 receptor can modulate activities including, for example, drug-induced emesis and nociception, gut motility, peristalsis, visceral sensation, and secretion. Postsynaptic 5-HT3 receptors can mediate fast excitatory synaptic transmission in rat neocortical interneurons and amygdala, and in ferret visual cortex. 5-HT3 receptors are also present on presynaptic nerve terminals, where they are thought to mediate or modulate neurotransmitter release. 5-HT3 receptors can be found at the ends of afferent branches of the vagus nerve. The vagus nerve sends signals to the vomit center of the brain in the medulla oblongata and in the chemoreceptor trigger zone (CTZ) of the brain.

1. 5-HT3 Receptor Antagonists

The methods and pharmaceutical compositions of the present invention can include one or more 5-HT3 receptor antagonists. 5-HT3 antagonists that can be used in the methods and pharmaceutical compositions described herein include, for example, cilansetron, clozapine, dolasetron (Anzemet®), granisetron (Kytril®), ondansetron (Zofran®), alosetron (Lotronex®) azasetron, memantine, mianserin, mirtazapine, bemesetron (MDL-72222) cilansetron, lerisetron (F-0930-RS), lurosetron, palonosetron (Aloxi®), olanzapine, quetiapine, ramosetron (Nasea®), renzapride, tropisetron (Navoban®), zacopride, zatosetron (LY-277, 359). Galanolactone is also a 5-HT3 receptor antagonist. Cisapride, renzapride, and metoclopramide possess some antagonist effect at 5-HT3 receptors. 5-HT3 receptor antagonists can prevent serotonin from binding to 5-HT3 receptors. The 5-HT3 receptor antagonist can be any other 5-HT3 receptor antagonist containing imidazole, oxazole, thiazole, pyrazole, 3-pyrroline, or pyrrolidine in its structural formula.

5-HT3 receptor antagonists can be used to treat irritable bowel syndrome, nausea, vomiting, neuropsychiatric disorders, bulimia, fibromyalgia and rheumatic diseases.

In one embodiment, a pharmaceutical composition is provided comprising, consisting of, or consisting essentially of a 5-HT3 receptor antagonist. In another embodiment, a pharmaceutical composition is provided comprising a 5-HT3 receptor antagonist and one or more additional agents that can prevent or treat physical dependence and/or withdrawal symptoms associated with narcotic use. In another embodiment, a pharmaceutical composition is provided consisting of, or consisting essentially of a 5-HT3 receptor antagonist and one, two, three, four, or five additional agents that can prevent or treat physical dependence and/or withdrawal symptoms associated with narcotic use.

In one embodiment, the pharmaceutical compositions of the present invention include one or more 5-HT3 receptor antagonists and one or more narcotics. A pharmaceutical composition is provided comprising, consisting of, or consisting essentially of a narcotic, a 5-HT3 receptor antagonist, and one or more additional agents that can prevent or treat physical dependence and/or withdrawal symptoms associated with narcotic use.

In another embodiment, a method for preventing or treating physical dependence and/or withdrawal symptoms associated with narcotic use in a subject is provided comprising, consisting of, or consisting essentially of administering to the subject a 5-HT3 antagonist. In another embodiment, a method for preventing or treating physical dependence and/or withdrawal symptoms associated with narcotic use in a subject is provided comprising, consisting of, or consisting essentially of administering to the subject a narcotic and a 5-HT3 antagonist. In another embodiment, a method for preventing or treating physical dependence and/or withdrawal symptoms associated with narcotic use in a subject is provided comprising, consisting of, or consisting essentially of administering to the subject a 5-HT3 antagonist and one or more additional agents that can reduce or treat physical dependence and/or withdrawal symptoms associated with narcotic use. In another embodiment, a method for preventing or treating physical dependence and/or withdrawal symptoms associated with narcotic use in a subject is provided comprising, consisting of, or consisting essentially of administering to the subject a narcotic, a 5-HT3 antagonist, and one or more additional agents that can reduce or treat physical dependence and/or withdrawal symptoms associated with narcotic use. In another embodiment, the methods of the present invention can include co-administering one or more 5-HT3 receptor antagonists with one or more narcotics to a subject. In another embodiment, the methods of the present invention can include administering to a subject a pharmaceutical composition including one or more 5-HT3 receptor antagonists and one or more narcotics.

2. Other Types of 5-HT3 Receptor Inhibitors

The methods and pharmaceutical compositions of the present invention can include other molecules that target 5-HT3 receptors. These molecules can include, for example nucleic acids, including siRNA, shRNA, miRNA, ribozymes, and proteins, including antibodies and enzymes. In one embodiment, a method of preventing or treating physical dependence and/or withdrawal symptoms associated with use of a narcotic in a subject is provided comprising administering a molecule comprising an siRNA, shRNA, miRNA, ribozyme, and/or protein that targets a 5-HT3 receptor or component of a 5-HT3 receptor to the subject. The molecule can be in a pharmaceutical composition comprising one or more additional agents that prevent or treat physical dependence and/or withdrawal symptoms associated with use of a narcotic B. Other Receptors that Regulate Emesis Another receptor involved in the regulation of emesis is the NK1 receptor. The NK1 receptor is a tachykinin receptor that is a member of the 7 transmembrane GPCR family of receptors. Activation of the NK1 receptor can induce activation of phospholipase C, which produces inositol triphosphate. NK1 receptor can bind to substance P, an 11-amino acid polypeptide that can function as a neurotransmitter and as a neuromodulator. The vomiting center in the brainstem contains high concentrations of substance P and NK1 receptor. In one embodiment, a method of treating or preventing physical dependence and/or withdrawal symptoms is provided comprising, consisting of, or consisting essentially of targeting an NK1 receptor.

Another receptor involved in the regulation of emesis is the dopamine D2 receptor. The dopamine D2 receptor is one of five subtypes of dopamine receptors. D1 and D5 receptors are members of the D1-like family of dopamine receptors, whereas D2, D3, and D4 receptors are members of the D2-like family. Dopamine receptors are GPCRs. In another embodiment, a method of treating or preventing physical dependence and/or withdrawal symptoms is provided comprising, consisting of, or consisting essentially of targeting a dopamine receptor.

C. Other Antiemetic Drugs

The methods and pharmaceutical compositions of the present invention can include agents that target other receptors or pathways that control emesis in addition to the 5-HT3 receptor. In one embodiment, a method of preventing or treating physical dependence and/or withdrawal symptoms associated with narcotic use in a subject is provided comprising, consisting of, or consisting essentially of targeting a pathway with an agent that regulates emesis. The agents can include antiemetic drugs. These drugs can include, for example:

H1 antihistamines, for example, dimenhydrinate (Dramamine®), several clizines (e.g., cyclizine, meclizine), diphenhydramine (Benadryl®), promethazine (Pentazine®, Phenergan®, Promacot®), and hydroxyzine (Vistaril®).

The drugs can include NK1 receptor antagonists, for example, Aprepitant (Emend®), Casopitant (Rezonic, Zunrisa®), Fosaprepitant (Emend® for Injection, Ivemend®), and Maropitant (Cerenia®).

The drugs can include dopamine antagonists, for example, chlorpromazine, droperidol (Inapsine®), prochlorperazine, metoclopramide, fluphenzine, domperidone, haloperidol, promethazine, and alizapride.

The drugs can include muscarinic receptor antagonists (anticholinergics), for example, hyoscine (scopolamine).

The drugs can include benzodiazepines, for example, midazolam, diazepam (Valium®) and lorazepam (Ativan®).

The drugs can include corticosteroids, for example, dexamethasone and methylprednisolone.

The drugs can include cannabinoids, for example, cannabis, dronabinol (Marinol®), nabilone (Cesamet®), and sativex.

The drugs can include, for example, benzquinamide, diphenidol (Vontrol®), trimethobenzamide (Tigan®), verapamil (Calan®), ginger, emetrol, propofol, peppermint, muscimol, and ajwain.

Non-pharmaceutical therapies that can be antiemetic and can be used in the methods of the present invention include acupuncture and hypnosis.

Other agents that can be used in the methods and composition of the present invention to prevent or treat physical dependence and/or withdrawal symptoms associated with use of a narcotic include, for example, clonidine, buprenorphine, or methadone, naltrexone, naloxone, or suboxone (combination of buprenorphine and naloxone).

IV. Methods of Treatment

In one embodiment, a method is provided comprising, consisting of, or consisting essentially of administering one or more 5-HT3 receptor modulators to a subject before administration of a narcotic to the subject to treat or prevent narcotic physical dependence and/or withdrawal symptoms. In another embodiment, a method is provided comprising, consisting of, or consisting essentially of administering one or more 5-HT3 receptor modulators to a subject after administration of a narcotic to the subject to treat or prevent narcotic physical dependence and/or withdrawal symptoms. In another embodiment, a method is provided comprising, consisting of, or consisting essentially of co-administering or more 5-HT3 receptor modulators is co-administered to a subject with a narcotic to treat or prevent narcotic physical dependence and/or withdrawal symptoms. In another embodiment, the one or more 5-HT3 receptor modulators is a 5-HT3 receptor antagonist, including ondansetron or palonosetron. In another embodiment, the one or more 5-HT-3 receptor modulators and the narcotic are administered to a subject as a co-formulation. In another embodiment, a method of preventing or treating physical dependence and/or withdrawal symptoms associated with use of a narcotic in a subject is provided comprising administering to the subject an agent that modulates a 5-HT3 receptor and one or more other agents that can prevent or treat physical dependence and/or withdrawal symptoms associated with use of the narcotic. The agent that modulates a 5-HT3 receptor and the one or more other agents can be administered to a subject either 1) before a narcotic is administered to the subject, 2) after a narcotic is administered to the subject, or 3) co-administered with the narcotic to the subject. An agent that modulates a 5-HT3 receptor can be administered before the narcotic is administered to the subject and the one or more other agents can be administered after the narcotic is administered to the subject. An agent that modulates a 5-HT3 receptor can be administered after a narcotic has been administered to a subject, and the one or more other agents can be administered before the narcotic is administered to the subject.

In one embodiment, one or more 5-HT3 receptor modulators and one or more other antiemetic drugs are administered to a subject before administration of a narcotic to the subject to treat or prevent narcotic physical dependence and/or withdrawal symptoms. In another embodiment, one or more 5-HT3 receptor modulators and one or more other antiemetic drugs are administered to a subject after administration of a narcotic to the subject to treat or prevent narcotic physical dependence and/or withdrawal symptoms. In another embodiment, a one or more 5-HT3 receptor modulators and one or more other antiemetic drugs are co-administered to a subject with a narcotic to treat or prevent narcotic physical dependence and/or withdrawal symptoms. In another embodiment, the one or more 5-HT3 receptor modulators is a 5-HT3 receptor antagonist, including ondansetron or palonosetron. In another embodiment, the one or more other antiemetic drugs include an antihistamine, a NK1 receptor antagonist, a muscarinic receptor antagonist, a benzodiazepine, a corticosteroid, and/or a cannabinoid. In another embodiment, the narcotic is morphine. In another embodiment, the one or more 5-HT3 receptor modulators and one or more other antiemetic drugs are administered to a subject as a co-formulation. In another embodiment, the one or more 5-HT-3 receptor modulators, one or more other antiemetic drugs, and one or more narcotics are administered to a subject as a co-formulation.

In one embodiment, one or more 5-HT3 receptor modulators and one or more antihistamines are administered to a subject to treat or prevent narcotic physical dependence and/or withdrawal symptoms. In another embodiment, the one or more 5-HT3 receptor modulators is a 5-HT3 antagonist. In another embodiment, the one or more 5-HT3 antagonists are selected from the group of cilansetron, clozapine, dolasetron (Anzemet®), granisetron (Kytril®), ondansetron (Zofran®), alosetron (Lotronex®) azasetron, memantine, mianserin, mirtazapine, bemesetron (MDL-72222) cilansetron, lerisetron (F-0930-RS), lurosetron, palonosetron (Aloxi®), olanzapine, quetiapine, ramosetron (Nasea®), renzapride, tropisetron (Navoban®), zacopride, zatosetron (LY-277, 359), Galanolactone Cisapride, renzapride, and metoclopramide. In another embodiment, the one or more 5-HT3 antagonist is ondansetron or palonosetron. In another embodiment, the one or more antihistamines are selected from the group of dimenhydrinate (Dramamine®), several clizines (e.g., cyclizine, meclizine), diphenhydramine (Benadryl®), promethazine (Pentazine®, Phenergan®, Promacot®), and hydroxyzine (Vistaril®). In another embodiment, the one or more antihistamines includes hydroxyzine. In one embodiment, the one or more 5-HT3 antagonists includes ondasetron and the antihistamine includes hydroxyazine. In another embodiment, the one or more 5-HT3 antagonists includes palonosetron and the antihistamine includes hydroxyazaine. In one embodiment, one or more 5-HT3 antagonists and one or more antihistamines are administered to a subject before a narcotic is administered to the subject to treat or prevent narcotic physical dependence and/or withdrawal symptoms. In another embodiment, one or more 5-HT3 antagonists and one or more antihistamines are administered to a subject after a narcotic is administered to the subject to treat or prevent narcotic physical dependence and/or withdrawal symptoms. In another embodiment, one or more 5-HT3 antagonists and one or more antihistamines are co-administered to a subject with one or more narcotics to treat or prevent narcotic physical dependence and/or withdrawal symptoms.

In another embodiment, one or more 5-HT3 antagonists and one or more NK1 receptor antagonists are administered to a subject to treat or prevent narcotic physical dependence and/or withdrawal symptoms. In another embodiment, one or more 5-HT3 antagonists and one or more dopamine antagonists are administered to a subject to treat or prevent narcotic physical dependence and/or withdrawal symptoms. In another embodiment, one or more 5-HT3 antagonists and one or more muscarinic receptor antagonists are administered to subject to treat or prevent narcotic physical dependence and/or withdrawal symptoms. In another embodiment, one or more 5-HT3 antagonists and one or more benzodiazepines are administered to a subject to treat or prevent narcotic withdrawal symptoms. In another embodiment, one or more 5-HT3 antagonists and one or more corticosteroids are administered to a subject to treat or prevent narcotic physical dependence and/or withdrawal symptoms. In another embodiment, one or more 5-HT3 antagonists and one or more cannabinoids are administered to a subject to treat or prevent narcotic physical dependence and/or withdrawal symptoms. In another embodiment, each of these combinations can be administered before a narcotic is administered to the subject or after a narcotic has been administered to the subject. In another embodiment, each of these combinations can be co-administered with a narcotic to the subject.

In one aspect, a method for treating addiction to a narcotic in a subject is provided comprising, consisting of, or consisting essentially of administering to the subject one or more agents that modulate a 5-HT3 receptor. In another embodiment, a method for treating addition to a narcotic in a subject is provided comprising, consisting of, or consisting essentially of administering to the subject one or more agents that modulate a 5-HT3 receptor and a second agent. In another embodiment, the agent that modulates a 5-HT3 receptor is a 5-HT3 antagonist. In another embodiment, the second agent is an antihistamine, a NK1 receptor antagonist, a muscarinic receptor antagonist, a benzodiazepine, a corticosteroid, and/or a cannabinoid. In one embodiment, the 5-HT3 antagonist is ondansetron and palonosetron. In one embodiment, the antihistamine is hydroxyzine.

In another aspect, a pharmaceutical composition comprising, consisting of, or consisting essentially of a narcotic and one or more agents that reduce physical dependence and/or withdrawal symptoms associated with use of the narcotic is provided. The one or more agents that reduce physical dependence and/or withdrawal symptoms associated with use of the narcotic can be an agent that modulates a 5-HT3 receptor an antihistamine, a NK1 receptor antagonist, a muscarinic receptor antagonist, a benzodiazepine, a corticosteroid, and/or a cannabinoid. In one embodiment, the agent that modulates a 5-HT3 receptor is a 5-HT3 receptor antagonist.

V. Formulations, Routes of Administration, and Effective Doses

The present invention includes methods and pharmaceutical compositions that comprise an agent or agents of the present invention. Furthermore, the present invention relates to formulations of these compositions and effective doses of the compositions. The pharmaceutical compositions can be used to reduce, prevent, or treat physical dependence and/or withdrawal symptoms associated with narcotic use. The pharmaceutical compositions can be used to reduce, prevent, or treat addiction associated with narcotic use.

The agents or their pharmaceutically acceptable salts may be provided alone or in combination with one or more other agents or with one or more other forms. For example a formulation may comprise consist of, or consist essentially of one or more agents in particular proportions, depending on the relative potencies of each agent and the intended indication. For example, in compositions that target two different targets, and where potencies are similar, about a 1:1 ratio of agents may be used. The two forms may be formulated together, in the same dosage unit e.g., in one cream, suppository, tablet, capsule, aerosol spray, or packet of powder to be dissolved in a beverage; or each form may be formulated in a separate unit, e.g., two creams, two suppositories, two tablets, two capsules, a tablet and a liquid for dissolving the tablet, two aerosol sprays, or a packet of powder and a liquid for dissolving the powder, etc.

A "pharmaceutically acceptable salt" can be a salt that retains the biological effectiveness and properties of the agents used in the present invention, and which are not biologically or otherwise undesirable. For example, a pharmaceutically acceptable salt does not interfere with the beneficial effect of an agent of the invention in modulating a 5-HT3 receptor.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present invention, and which are not biologically or otherwise undesirable. For example, the ester or amide does not interfere with the beneficial effect of an agent of the invention in modulating a 5-HT3 receptor. Typical esters include ethyl, methyl, isobutyl, ethylene glycol, and the like. Typical amides include unsubstituted amides, alkyl amides, dialkyl amides, and the like.

In some embodiments, an agent can be administered in combination with one or more other compounds, forms, and/or agents, e.g., as described above. The agent can be a narcotic. Pharmaceutical compositions comprising combinations of a 5-HT3 receptor modulator with one or more other active agents can be formulated to comprise certain molar ratios. For example, molar ratios of about 99:1 to about 1:99 of a 5-HT3 receptor modulator to the other active agent can be used. In some subset of the embodiments, the range of molar ratios of the 5-HT3 receptor modulator: other active agent is selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of 5-HT3 receptor modulator: other active agent may be about 1:9, and in some embodiments may be about 1:1. In one embodiment, the molar ratio of a 5-HT3 receptor modulator to narcotic is about 1:100, 1:50, 1:25, 1:10, 1:9, 1:8, 1:7, 1:6, 1:5, 1:4, 1:3, 2:5, 1:2, 1:1, 2:1, 5:2, 3:1, 4:1, 5; 1, 6:1, 7:1, 8:1, 9:1, 10:1, 25:1, 50:1, or 100:1. The two agents (e.g., 5-HT3 receptor modulator and narcotic), forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc. In one embodiment, the 5-HT3 receptor modulator is a 5-HT3 receptor antagonist. In another embodiment, the narcotic is morphine. In another embodiment, the 5-HT3 receptor modulator is a 5-HT3 antagonist and the narcotic is morphine. In another embodiment, the 5-HT3 antagonist is ondansetron or palonosetron and the narcotic is morphine.

In one embodiment, a composition is provided comprising, consisting of, or consisting essentially of a 5-HT3 receptor modulator and another active agent. In one embodiment, the other active agent is another antiemetic. In another embodiment the molar ratio between the 5-HT3 receptor modulator and the other active agent is about 1:100, 1:50, 1:25, 1:10, 1:5, 1:4, 1:3, 2:5, 1:2, 1:1, 2:1, 5:2, 3:1, 4:1, 5:1, 10:1, 25:1, 50:1, or 100:1. In another embodiment, the 5-HT3 receptor modulator is a 5-HT3 receptor antagonist. In another embodiment, the 5-HT3 receptor modulator is a 5-HT3 receptor antagonist and the other antiemetic is an antihistamine. In another embodiment, the 5-HT3 receptor modulator and other antiemetic are formulated together, in the same dosage unit e.g., in one cream, suppository, tablet, capsule, or packet of powder to be dissolved in a beverage; or each agent, form, and/or compound may be formulated in separate units, e.g., two creams, suppositories, tablets, two capsules, a tablet and a liquid for dissolving the tablet, an aerosol spray a packet of powder and a liquid for dissolving the powder, etc.

The agents and/or combinations of agents can be administered with still other agents. The choice of agents that can be co-administered with the agents and/or combinations of agents of the instant invention can depend, at least in part, on the condition being treated. Agents of particular use in the formulations of the present invention include, for example, any agent having a therapeutic affect on physical dependence or withdrawal symptoms of a narcotic user or narcotic addiction.

In one embodiment, a composition is provided comprising a 5-HT3 receptor modulator, a second agent, and a narcotic. In another embodiment, the second agent is an antiemetic.

In one embodiment, a pharmaceutical composition does not comprise a stimulant. In another embodiment, a pharmaceutical composition does not comprise an opioid antagonist. In another embodiment, a pharmaceutical composition does not comprise an NSAID analgesic. In another embodiment, a pharmaceutical composition does not comprise an NMDA receptor antagonist. In another embodiment, a pharmaceutical composition does not comprise a Cox-2 inhibitor. In another embodiment, a pharmaceutical composition does not comprise a beta blocker, a serotonin receptor agonist, a vasconstrictor, an anti-platelet agent, and anti-convulsant, triptan, ergot, or calcitonin-gene-related peptide receptor antagonist, an anti-depressant, and anticholinergic agent, an anesthetic agent, or an $\alpha_2$ adrenoreceptor agonist agent. In another embodiment, a pharmaceutical composition is not in the form of a bilayer tablet. In another embodiment, a pharmaceutical composition is in the form of a bilayer tablet.

A pharmaceutical composition, as used herein, can be any composition prepared for administration to a subject. The agents (or pharmaceutically acceptable salts, esters, or amides thereof) can be administered in a form wherein the active agent(s) are a mixture or admixture with one or more pharmaceutically acceptable carriers. The pharmaceutical compositions can be administered to a subject using routes that include, for example, oral, buccal, topical, rectal, transdermal, transmucosal, subutaneous, intravenous, intramuscular, and nasal. Pharmaceutical compositions for use in accordance with the present invention can be formulated using one or more physiologically acceptable carriers, comprising excipients, diluents, and/or auxiliaries, which facilitate processing of the active agent(s) into preparations that can be administered. Proper formulation of the pharmaceutical composition can depend, at least in part, on the route of administration.

In some embodiments, one or more agents can be co-administered with one or more narcotics to reduce physical dependence and/or withdrawal symptoms associated with use of the one or more narcotics.

A. Routes of Administration

1. Oral Administration

For oral administration of an agent(s), the pharmaceutical composition can be formulated by combining the active agent(s) with pharmaceutically acceptable carriers that are well known in the art. Formulations can comprise pharmaceutically acceptable carriers including solid diluents or fillers, sterile aqueous media, and various non-toxic organic solvents. The carriers can enable the agent(s) of the invention to be formulated as tablets, including chewable tablets, pills, dragees, capusules, lozenges, hard candy, liquids, gels, syrups, slurries, powders, suspensions, elixirs, wafers, and the like, for oral administration to the subject. Generally, the agent(s) of the invention will be included at concentration levels ranging from about 0.5%, about 5%, about 10%, about 20%, about 30% to about 50%, about 60%, about 70%, about 80%, or about 90% by weight of the total composition or oral dosage forms, in an amount sufficient to provide a desired dosage unit.

The agent(s) of this invention can be in aqueous suspension for oral use. The aqueous suspension can include pharmaceutically acceptable excipients, such as a suspending agent (e.g., methyl cellulose), a wetting agent (e.g., lecithin, lysolecithin and/or a long-chain fatty alcohol), as well as coloring agents, preservatives, flavoring agents, etc.

In some embodiments, non-aqueous solvents or oils may be used to bring agent(s) into solution owing to, for example, the presence of large lipophilic moieties. Alternatively, emulsions, suspensions, or other preparations, for example, liposomal preparations, can be used. Any methods known to those skilled in the art can be used for preparing liposomal preparations (see, e.g., Bangham et al., J. Mol. Biol. 23: 238-252 (1965) and Szoka et al., Proc. Natl. Acad. Sci. USA 75: 4194-4198 (1978)). Ligands can also be attached to the liposome to direct these compositions to particular sites of action. Agents of this invention can also be integrated into foodstuffs, for example, butter, cream cheese, ice cream, or salad dressing to facilitate solubilization, administration, and/or compliance in certain subject populations.

Pharmaceutical compositions for oral administration can be generated as a solid excipient, by grinding a resulting mixture and processing the mixture of granules, after adding suitable auxiliaries, to obtain tablets or dragee cores. Suitable excipients can include, for example, fillers such as sugars, including lactose, mannitol, sucrose, or sorbitol; flavoring elements, cellulose prepartions such as, or example, maize starch, wheat starch, rice starch, potato starch, gelatin, gum tragacanth, methyl cellulose, hydroxyproplymethyl-cellulose, sodium carboxymethylcelulose, and/or polyvinyl pyrrolidone (PVP). Disintegrating agents can be added, such as the cross-linked polyvinyl pyrrolidone, agar, or alginic acid or a salt thereof such as sodium alginate. The agents can also be formulated as a sustained release preparation.

Suitable coatings can be provided for dragee cores; for example, concentrated sugar solutions can be used, which can contain gum arabic, talc, polyvinyl pyrrolidone, carbopol gel, polyethyleene glycol, and/or titanium dioxide, lacquer solutions, and suitable organic solvents or solvent mixtures. Dyestuffs or pigments can be added to the tablets or dragée coatings, for example, to allow for identification or to characterize different combinations of active agents.

Pharmaceutical preparations that can be used orally include push fit capsules made of gelatin, as well as soft, sealed capsules made of gelatin and a plasticizer, such as glycerol or sorbitol. The push fit capsules can contain the active agent(s) in admixture with filler such as lactose, binders such as starches, and/or lubricants such as talc or magnesium stearate and, optionally, stabilizers. In soft capsules, the active agents can be dissolved or suspended in suitable liquids, such as fatty oils, liquid paraffin, or liquid polyethylene glycols. In addition, stabilizers may be added. All formulations for oral administration can be in dosages suitable for administration.

2. Injection and Topical Application

For injection, the agents of the present invention can be formulated in aqueous solutions, including but not limited to physiologically compatible buffers such as Hank's solution, Ringer's solution, or physiological saline buffer. Such compositions may also include one or more excipients, for example, preservatives, solubilizers, fillers, lubricants, stabilizers, albumin, and the like. Methods of formulation are known in the art, for example, as disclosed in Remington's Pharmaceutical Sciences, latest edition, Mack Publishing Co., Easton P.

The agent(s) can also be formulated as a depot preparation, a dosage form of drug than can act over a period of time by controlled-release processes. A depot preparation can be administered by implantation or transcutaneous delivery (for example, subcutaneously or intramuscularly), intramuscular injection or use of a transdermal patch. Thus, for example, the agent(s) may be formulated with suitable polymeric or hydrophobic materials (for example as an emulsion in an acceptable oil) or ion exchange resins, or as sparingly soluble derivatives, for example, as a sparingly soluble salt.

In some embodiments, pharmaceutical compositions comprising one or more agents of the present invention exert local and regional effects when administered topically or injected at or near particular sites of infection. Direct topical application, e.g., of a viscous liquid, gel, jelly, cream, lotion, ointment, suppository, foam, or aerosol spray, may be used for local administration, to produce for example local and/or regional effects. Pharmaceutically appropriate vehicles for such formulation include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983.

Pharmaceutical compositions of the present invention can contain a cosmetically or dermatologically acceptable carrier. Such carriers are compatible with skin, nails, mucous membranes, tissues and/or hair, and can include any conventionally used cosmetic or dermatological carrier meeting these requirements. Such carriers can be readily selected by one of ordinary skill in the art. In formulating skin ointments, an agent or combination of agents of the instant invention may be formulated in an oleaginous hydrocarbon base, an anhydrous absorption base, a water-in-oil absorption base, an oil-in-water water-removable base and/or a water-soluble base.

The compositions according to the present invention can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. Other than the agents of the invention, the amounts of the various constituents of the compositions according to the invention are those conventionally used in the art. These compositions in particular constitute protection, treatment or care creams, milks, lotions, gels or foams for the face, for the hands, for the body and/or for the mucous membranes, or for cleansing the skin. The compositions may also consist of solid preparations constituting soaps or cleansing bars.

Compositions of the present invention can also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants may be introduced into the fatty phase, into the aqueous phase and/or into the lipid vesicles.

In some embodiments, ophthalmic solutions, suspensions, ointments or inserts comprising an agent or combination of agents of the present invention can be used.

In some embodiments, otic solutions, suspensions, ointments or inserts comprising an agent or combination of agents of the present invention can be used.

In some embodiments, the agent(s) of the present invention are delivered in soluble rather than suspension form, which allows for more rapid and quantitative absorption to the sites of action. In general, formulations such as jellies, creams, lotions, suppositories and ointments can provide an area with more extended exposure to the agents of the present invention, while formulations in solution, e.g., sprays, provide more immediate, short-term exposure.

In some embodiments relating to topical/local application, the pharmaceutical compositions can include one or more penetration enhancers. For example, the formulations may comprise suitable solid or gel phase carriers or excipients that increase penetration or help delivery of agents or combinations of agents of the invention across a permeability barrier, e.g., the skin. Many of these penetration-enhancing compounds are known in the art of topical formulation, and include, e.g., water, alcohols (e.g., terpenes like methanol, ethanol, 2-propanol), sulfoxides (e.g., dimethyl sulfoxide, decylmethyl sulfoxide, tetradecylmethyl sulfoxide), pyrrolidones (e.g., 2-pyrrolidone, N-methyl-2-pyrrolidone, N-(2-hydroxyethyl)pyrrolidone), laurocapram, acetone, dimethylacetamide, dimethylformamide, tetrahydrofurfuryl alcohol, L-α-amino acids, anionic, cationic, amphoteric or nonionic surfactants (e.g., isopropyl myristate and sodium lauryl sulfate), fatty acids, fatty alcohols (e.g., oleic acid), amines, amides, clofibric acid amides, hexamethylene lauramide, proteolytic enzymes, α-bisabolol, d-limonene, urea and N,N-diethyl-m-toluamide, and the like. Additional examples include humectants (e.g., urea), glycols (e.g., propylene glycol and polyethylene glycol), glycerol monolaurate, alkanes, alkanols, ORGELASE, calcium carbonate, calcium phosphate, various sugars, starches, cellulose derivatives, gelatin, and/or other polymers. In some embodiments, the pharmaceutical compositions will include one or more such penetration enhancers.

In some embodiments, the pharmaceutical compositions for local/topical application can include one or more antimicrobial preservatives such as quaternary ammonium compounds, organic mercurials, p-hydroxy benzoates, aromatic alcohols, chlorobutanol, and the like.

Orally- or rectally delivered solutions, suspensions, ointments, enemas and/or suppositories comprising an agent or combination of agents of the present invention can be used.

3. Inhalation

Aerosol solutions, suspensions or dry powders comprising an agent or combination of agents of the present invention can be used. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a 5-HT3 receptor modulator can be dissolved, suspended or emulsified in a propellant or a mixture of solvent and propellant, e.g., for administration as a nasal spray or inhalant. Aerosol formulations may contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that the agent or combination of agents of the present invention is carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants useful in the present invention include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, issued Dec. 27, 1994; Byron et al., U.S. Pat. No. 5,190,029, issued Mar. 2, 1993; and Purewal et al., U.S. Pat. No. 5,776,434, issued Jul. 7, 1998. Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as the ethers. An aerosol formulation of the invention can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present invention can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of an agent of the invention such as a 5-HT3 receptor modulator and/or an antihistamine and/or a narcotic in (substantially) pure propellant or as a mixture of propellant and solvent. The solvent can be used to dissolve the agent and/or retard the evaporation of the propellant. Solvents useful in the invention include, for example, water, ethanol and glycols. Any combination of suitable solvents can be use, optionally combined with preservatives, antioxidants, and/or other aerosol components.

An aerosol formulation can also be a dispersion or suspension. A suspension aerosol formulation can comprise a suspension of an agent or combination of agents of the instant invention, e.g., 5-HT3 modulator, and a dispersing agent. Dispersing agents useful in the invention include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water and a propellant, as well as an agent or combination of agents of the invention, e.g., a 5-HT3 receptor modulator. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

B. Effective Dosage

Pharmaceutical compositions suitable for use in the present invention include compositions wherein the active ingredients are present in an effective amount, i.e., in an amount effective to achieve therapeutic benefit in a subject. The actual amount effective for a particular application will depend on the condition or conditions being treated, the condition of the subject, the formulation, and the route of administration, as well as other factors known to those of skill in the art. Determination of an effective amount of, for example, a 5-HT3 receptor modulator, a narcotic, or an antihistamine, is well within the capabilities of those skilled in the art, in light of the disclosure herein, and will be determined using routine optimization techniques.

The effective amount for use in humans can be determined from animal models. For example, a dose for humans can be formulated to achieve circulating, liver, topical and/or gastrointestinal concentrations that have been found to be effective in animals. One skilled in the art can determine the effective amount for human use, especially in light of the animal model experimental data described herein. Based on animal data, and other types of similar data, those skilled in the art can determine the effective amounts of compositions of the present invention appropriate for humans.

The effective amount when referring to an agent or combination of agents of the invention will generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

In one embodiment, a pharmaceutical composition for treating or preventing physical dependence and/or withdrawal symptoms associated with use of a narcotic is provided comprising a 5-HT3 receptor modulator.

In another embodiment, the 5-HT3 receptor modulator is ondansetron. In another embodiment, the amount of ondansetron in a dose of the pharmaceutical composition is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg. In one embodiment, amount of ondansetron in a dose of the pharmaceutical composition is about 1-20 mg, about 5-10 mg, about 8-16 mg, or about 4-8 mg.

In another embodiment, a dosage form comprises, consists of, or consists essentially of up to 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg ondansetron per dose.

In another embodiment, an a method comprises, consists of, or consists essentially of administering up to 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg ondansetron to a subject.

In another embodiment, the 5-HT3 receptor modulator is palonosetron. In another embodiment, the amount of palonosetron in a dose of the pharmaceutical composition is about 0.01 mg, about 0.02 mg, about 0.03 mg, about 0.04 mg, about 0.05 mg, about 0.06 mg, about, 0.07 mg, about 0.075 mg, about, 0.8 mg, about 0.9 mg, about 0.1 mg, about 0.2 mg, about 0.3 mg, about 0.4 mg, about 0.5 mg, about 0.6 mg., about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, or about 2.0 mg. In another embodiment, the amount of palonosetron in the pharmaceutical composition is about 0.01 to about 0.1 mg, 0.1 to 1.0 mg, about 0.5 to 1.0 mg, about 0.5-2.0 mg, or about 1.0 to 2.0 mg.

In another embodiment, a dosage form comprises, consists, or consists essentially of up to 0.01 mg, 0.02 mg, 0.03 mg, 0.04 mg, 0.05 mg, 0.06 mg, 0.07 mg, 0.075 mg, 0.08 mg, 0.09 mg, 0.1 mg, 0.2 mg, 0.3 mg, 0.4 mg, 0.5 mg, 0.6 mg., 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg palonosetron per dose.

In another embodiment, a method comprises, consists, or consists essentially of administering up to 0.01 mg, 0.02 mg, 0.03 mg, 0.04 mg, 0.05 mg, 0.06 mg, 0.07 mg, 0.075 mg, 0.08 mg, 0.09 mg, 0.1 mg, 0.2 mg, 0.3 mg, 0.4 mg, 0.5 mg, 0.6 mg., 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg palonesetron to a subject.

In another embodiment, the pharmaceutical composition further comprises a narcotic. In one embodiment, the narcotic is morphine. In another embodiment, the amount of morphine in a dose of the pharmaceutical composition is about 0.1 mg, about 0.2 mg, about 0.5 mg, about 0.75 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, or about 60 mg. In another embodiment, the amount of morphine in a dose is about 10-20 mg/70 kg of subject. In another embodiment, the amount of morphine in a dose is about 5-15 mg/70 kg of subject. In another embodiment, the amount of morphine in a dose is about 1-10 mg, about 5-15 mg, about 10-20 mg, about 20-50 mg, or about 2-25 mg.

In one embodiment, a dosage form comprises, consists of, or consists essentially of up to 0.1 mg, 0.2 mg, 0.5 mg, 0.75 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, or 60 mg morphine per dose. In another embodiment, the amount of morphine in a dosage form is about 10-20 mg/70 kg of subject. In another embodiment, the amount of morphine in a dosage form is about 5-15 mg/70 kg of subject.

In another embodiment, the amount of morphine in a dosage form is about 1-10 mg, about 5-15 mg, about 10-20 mg, about 20-50 mg, or about 2-25 mg.

In one embodiment, a method comprises, consists of, or consists essentially of administering up to 0.1 mg, 0.2 mg, 0.5 mg, 0.75 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, or 60 mg of morphine to a subject. In another embodiment, the amount of morphine administered to a subject is about 10-20 mg/70 kg of subject. In another embodiment, the amount of morphine administered to a subject is about 5-15 mg/70 kg of subject. In another embodiment, the amount of morphine administered to a subject is about 1-10 mg, about 5-15 mg, about 10-20 mg, about 20-50 mg, or about 2-25 mg.

In another embodiment, the pharmaceutical composition further comprises an antihistamine. In one embodiment, the antihistamine is hydroxyzine (Vistaril). In another embodiment, the amount of hydroxyzine in a dose of the pharmaceutical composition is about 5 mg, about 7.5 mg, about 10 mg, about 12.5 mg, about 15 mg, about 17.5 mg, about 20 mg, about 22.5 mg, about 25 mg, about 27.5 mg, about 30 mg, about 32.5 mg, about 35 mg, about 37.5 mg, about 40 mg, about 42.5 mg, about 45 mg, about 47.5 mg, about 50 mg, about 52.5 mg, about 55 mg, about 57.5 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, or about 150 mg. In another embodiment, the amount of hydroxyzine in a dose of the pharmaceutical composition is about 10-50 mg, about 50-100 mg, or about 10-25 mg.

In another embodiment, a method comprises, consists of, or consists essentially of administering up to 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 65 mg, 70 mg, 75 mg, 80 mg, 85 mg, 90 mg, 95 mg, 100 mg, 110 mg, 120 mg, 130 mg, 140 mg, or 150 mg hydroxyzine. In another embodiment, a dosage form comprises, consists of, or consists essentially of up to 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 65 mg, 70 mg, 75 mg, 80 mg, 85 mg, 90 mg, 95 mg, 100 mg, 110 mg, 120 mg, 130 mg, 140 mg, or 150 mg hydroxyzine per dose.

In one embodiment, about 100 mg hydroxyzine and about 0.75 mg palonosetron are administered to a subject. In another embodiment, up to 200 mg hydroxyzine and up to 1.5 mg palonosetron are administered to a subject.

In another embodiment, a dosage form has up to 200 mg hydroxyzine and up to 1.5 mg palonosetron per dose. In another embodiment, a dosage form has less than 150 mg hydroxyzine and less than 1.5 mg of palonosetron per dose.

In another embodiment a dosage form comprises, consists of, or consists essentially of up to 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, or 20 mg ondansetron per dose and up to 0.1 mg, 0.2 mg, 0.5 mg, 0.75 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, or 60 mg morphine per dose.

In another embodiment, a dosage form comprises, consists of, or consists essentially of up to 0.1 mg, 0.2 mg, 0.5 mg, 0.75 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, or 60 mg morphine per dose and up to 0.01 mg, 0.02 mg, 0.03 mg, 0.04 mg, 0.05 mg, 0.06 mg, 0.07 mg, 0.075 mg, 0.08 mg, 0.09 mg, 0.1 mg, 0.2 mg, 0.3 mg, 0.4 mg, 0.5 mg, 0.6 mg., 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg palonesetron per dose.

In another embodiment, a dosage form comprises, consists of, or consists essentially of up to 0.1 mg, 0.2 mg, 0.5 mg, 0.75 mg, 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, 55 mg, or 60 mg morphine per dose; up to 0.01 mg, 0.02 mg, 0.03 mg, 0.04 mg, 0.05 mg, 0.06 mg, 0.07 mg, 0.075 mg, 0.08 mg, 0.09 mg, 0.1 mg, 0.2 mg, 0.3 mg, 0.4 mg, 0.5 mg, 0.6 mg., 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg palonesetron per dose; and up to 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 65 mg, 70 mg, 75 mg, 80 mg, 85 mg, 90 mg, 95 mg, 100 mg, 110 mg, 120 mg, 130 mg, 140 mg, or 150 mg hydroxyzine per dose.

In another embodiment, a method of preventing of treating physical dependence and/or withdrawal symptoms is provided comprising, consisting of, or consisting essentially of administering to a subject up to 0.01 mg, 0.02 mg, 0.03 mg, 0.04 mg, 0.05 mg, 0.06 mg, 0.07 mg, 0.075 mg, 0.08 mg, 0.09 mg, 0.1 mg, 0.2 mg, 0.3 mg, 0.4 mg, 0.5 mg, 0.6 mg., 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2.0 mg palonesetron; and up to 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 65 mg, 70 mg, 75 mg, 80 mg, 85 mg, 90 mg, 95 mg, 100 mg, 110 mg, 120 mg, 130 mg, 140 mg, or 150 mg hydroxyzine.

Further, appropriate doses for a 5-HT3 receptor modulator can be determined based on in vitro experimental results. For example, the in vitro potency of an agent modulating a 5-HT3 receptor provides information useful in the development of effective in vivo dosages to achieve similar biological effects.

C. Administration Setting and Schedule

In some embodiments, administration of agents of the present invention can be intermittent, for example administration once every two days, every three days, every five days, once a week, once or twice a month, and the like. In some embodiments, the amount, forms, and/or amounts of the different forms may be varied at different times of administration.

In some embodiments, one or more agents that reduce physical dependence and/or withdrawal symptoms associated with use of a narcotic can be administered to a subject before the narcotic. The one or more agents can be administered at least 1, 5, 15, 30, 45, or 60 minutes before administration of the narcotic. The agent can be administered at least 2, 3, 4, 5, 6, 12, or 24 hours before administering the narcotic. In one embodiment, the one or more agents comprise a 5-HT3 receptor modulator. In another embodiment, the 5-HT3 receptor modulator is a 5-HT3 receptor antagonist. In one embodiment, the 5-HT3 antagonist is ondansetron and palonosetron. In another embodiment, the one or more agents comprises a 5-HT3 receptor modulator and a second antiemetic agent. In another embodiment, the second antiemetic agent is an antihistamine. In another embodiment, the antihistamine is hydroxyzine.

In some embodiments, one or more agents that reduce physical dependence and/or withdrawal symptoms associated with use of a narcotic can be administered after administering a narcotic to a subject. The one or more agents can be administered at least 1, 5, 15, 30, 45, or 60 minutes after administration of the narcotic to the subject. The one or more agents can be administered at least 2, 3, 4, 5, 6, 12, or 24 hours after administering the narcotic to the subject. The agent can be administered to the subject after at least 1, 2, 3, 4, or 5 doses of a narcotic have been administered to the subject. In one embodiment, the one or more agents comprise a 5-HT3 receptor modulator. In another embodiment, the 5-HT3 receptor modulator is a 5-HT3 receptor antagonist. In one embodiment, the 5-HT3 antagonist is ondansetron and palonosetron. In another embodiment, the one or more agents comprises a 5-HT3 receptor modulator and a second antiemetic agent. In another embodiment, the second antiemetic agent is an antihistamine. In another embodiment, the antihistamine is hydroxyzine.

In some embodiments, one or more agents that reduce physical dependence and/or withdrawal symptoms associated with use of a narcotic can be administered to a subject at the same time (co-administered) as the narcotic. The narcotic and the one or more agents can be in the same formulation. The narcotic and the one or more agents can be in different formulations. The narcotic and the one or more agents can be administered to the subject by the same route. The narcotic and the one or more agents can be administered to the subject by different routes. In one embodiment, the one or more agents comprise a 5-HT3 receptor modulator. In another embodiment, the 5-HT3 receptor modulator is a 5-HT3 receptor antagonist. In one embodiment, the 5-HT3 antagonist is ondansetron and palonosetron. In another embodiment, the one or more agents comprises a 5-HT3 receptor modulator and a second antiemetic agent. In another embodiment, the second antiemetic agent is an antihistamine. In another embodiment, the antihistamine is hydroxyzine.

In some embodiments, one or more agents that reduce physical dependence and/or withdrawal symptoms associated with use of a narcotic can be administered to a subject before an opioid antagonist is administered to the subject. The one or more agents can be administered at least 1, 5, 15, 30, 45, or 60 minutes before an opioid antagonist is administered to the subject. The one or more agents can be administered to the subject at least 2, 3, 4, 5, 6, 12, or 24 hours before administering the narcotic. In one embodiment, the one or more agents comprise a 5-HT3 receptor modulator. In another embodiment, the 5-HT3 receptor modulator is a 5-HT3 receptor antagonist. In one embodiment, the 5-HT3 antagonist is ondansetron and palonosetron. In another embodiment, the one or more agents comprises a 5-HT3 receptor modulator and a second antiemetic agent. In another embodiment, the second antiemetic agent is an antihistamine. In another embodiment, the antihistamine is hydroxyzine.

In one embodiment, the effective plasma concentration of an agent of the present invention, including for example, an antiemetic, 5-HT3 receptor antagonist, or antihistamine, can be reached in about 1 minute (min.), about 2 min., about 3 min., about 4 min., about 5 min., about 6 min., about 7 min., about 8 min., about 9 min., about 10 min., about 11 min., about 12 min., about 13 min., about 14 min., about 15 min., about 16 min., about 17 min., about 18 min., about 19 min., or about 20 minutes after administration to a subject.

The agent can be an agent that modulates a 5-HT3 receptor. The agent can by a 5-HT3 receptor antagonist. The agent and/or narcotic can be administered to a subject in a medical setting, for example, a clinic, hospital, etc. The agent and/or the narcotic can be administered to a subject by a health care provider, for example, a physician, nurse, etc.

EXAMPLES

Example 1

Genetic Variation within HTR3A Affects Morphine Dependence

Eighteen inbred strains were made physically dependent on morphine, an archetypical opioid narcotic, by administration over a 4-day period. Then, the jumping behavior precipitated by the administration of an opioid receptor antagonist (naloxone) to the dependent mice was measured. There were very large inter-stain differences in the withdrawal-induced jumping behavior; SM/J mice averaged only one jump in the 15 minute period following naloxone administration while BUB/BnJ mice jumped over 100 times under the same conditions (FIG. 1). Other investigators (Kest, B., et al., *Pharmacol Biochem Behav*, 2002. 73(4): p. 821-828) evaluated eight of these strains by a similar method, and a comparative Pearson correlation analysis of the data for the 8 common strains indicated that two studies yielded similar results (coefficient of 0.87, p=0.05).

Figure 2:
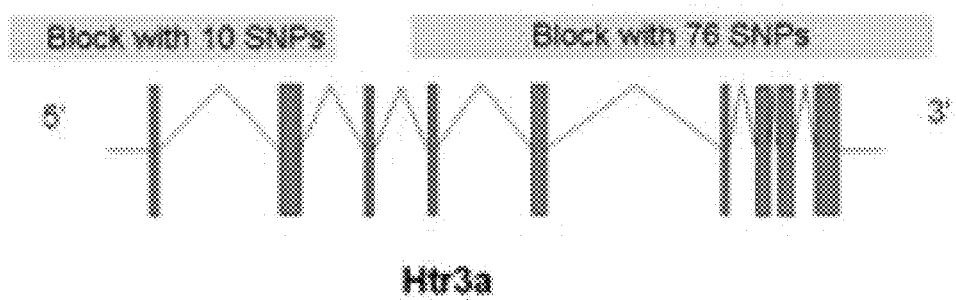
FIG. 2 is a diagram of the Htr3a gene and associated haplotypic blocks.
Figure 2:
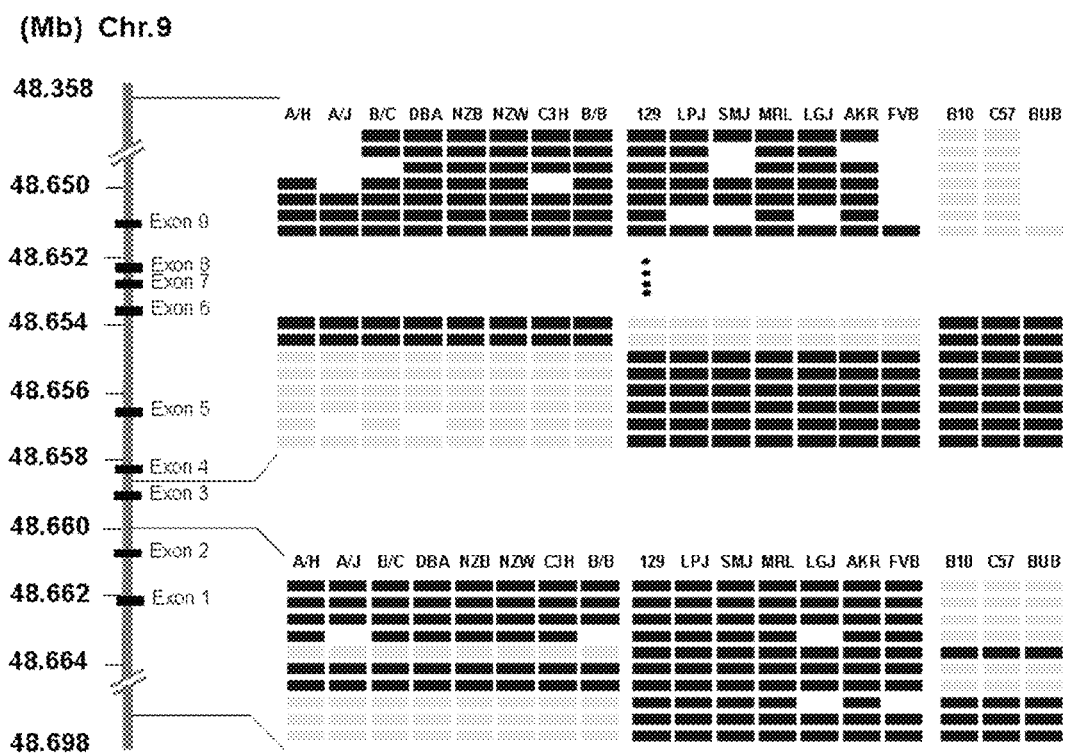

Haplotype-based computational genetic mapping was used to analyze data from our study (Wang, J., et al., *Trends Genet*, 2005. 21(9): p. 526-32; Liao, G., et al., *Science*, 2004. 306(5696): p. 690-695). The distribution of the naloxone-induced withdrawal behavior was compared with the pattern of genetic variation across the 18 strains analyzed. Interestingly, the two most highly correlated haplotype blocks (p-value<$5 \times 10^{-6}$) were in close proximity on chromosome 9 and corresponded to the 5' and 3' regions of the Htr3a gene (FIG. 1 and FIG. 2). There are seven haplotype blocks covering this gene though the dependence-associated blocks account for the majority of SNPs. The remaining small non-correlated blocks are located between the second and forth exons. None of the SNPs in the associated blocks alter the predicted amino acid sequence of the protein. This gene encodes the 5-HT3a receptor, which has well-established roles in modulating nausea, anxiety and pain (Costall, B. and R. J. Naylor, *Curr Drug Targets CNS Neurol Disord*, 2004. 3(1): p. 27-37). Although more speculative, it has also been postulated that this receptor could also affect opioid tolerance and dependence (Roychoudhury, M. and S. K. Kulkarni, *Methods Find Exp Clin Pharmacol*, 1996. 18(10): p. 677-83).

FIG. 1 shows computational genetic analysis of inter-strain differences in physical dependence on morphine. FIG. 1A shows eighteen strains (8 mice per strain) were treated for four days with morphine to establish physical dependence. On the fifth day, the number of jumps made during the 15-minute period after naloxone injection was measured as an indicator of the degree of opioid dependence. The data represent the mean number of jumps for each indicated strain+/−SEM (FIG. 1B). The morphine physical dependence data (mean number of jumps for each strain) was analyzed by computational genetic mapping. The ten most strongly correlated haplotype blocks are shown. For each block, the chromosomal location, number of SNPs within a block and its gene symbol are listed. For each gene, the haplotypes are represented by a colored block, and the blocks are presented in the same rank order as the phenotypic data. Strains sharing the same haplotype have the same colored block. The calculated p-value measures the probability that the strain groupings within a block would have the same degree of association with the phenotypic data by random chance. The genetic effect indicates the fraction of the inter-strain variance that is potentially attributable to the haplotype.

FIG. 2 shows a diagram of the Htr3a gene and associated haplotypic blocks. FIG. 2A illustrates the intron/exon structure of the Htr3a gene along with the relative positions of the two associated haplotypic blocks are displayed. The two haplotype blocks whose pattern of genetic correlation best correlated with the severity of the naloxone-precipitated jumping response are located at the 5' and 3' regions of the Htr3a gene. Each of these haplotype blocks has 3 different haplotypes, and none of the 86 SNPs within these 2 blocks alters the predicted amino acid sequence of the 5-HT3a receptor. (http://mouseSNP.roche.com). FIG. 2B shows that there are 7 haplotype blocks across the Htr3a gene. The two major blocks are the dependence correlated 3' and 5' blocks, each with 76 and 10 SNPs respectively, covering most of Htr3a gene. The other five small blocks (not shown in the figure) are between the 5' and 3' blocks (between exons 2 and 4) and contain a of total 15 SNPs. The 5' and 3' blocks, which exhibited the highest correlation with physical dependence on morphine, had the same pattern of genetic variation across the 18 strains of mice used in our studies.

Experimental details for this Example can be found in Example 9.

Example 2

5-HT3 Receptor Antagonist (Ondansetron) Decreases Naloxone Precipitated Withdrawal Behavior To determine whether 5-HT3 receptor function affects opioid withdrawal, the effect of a selective 5-HT3 receptor antagonist (ondansetron) on withdrawal-associated jumping was assessed. Administration of ondansetron prior to measurement of naloxone-induced jumping significantly reduced this response in morphine-dependent C57BL/6J mice in a dose-dependent fashion (FIG. 3A). In addition, simultaneous administration of ondansetron with each morphine dose during the 4-day protocol for establishing dependence diminished the naloxone-precipitated withdrawal response (FIG. 3B). The latter effect was unlikely to be due to the presence of residual ondansetron at the time of the dependence measurement since a 1 mg/kg dose was not able to effectively inhibit withdrawal when given acutely, and approximately 5 half-lives of the drug had passed in the time between the last dose of ondansetron and the naloxone-precipitated withdrawal procedure. Whether 5-HT3 receptors expressed within the CNS were capable of altering the severity of withdrawal was investigated next. In these experiments, ondansetron (or saline) was injected intra-cerebroventricularly (i.c.v.) before naloxone was administered to morphine-dependent C57BL6 mice. Intra-cerebroventricular administration of ondansetron profoundly blocked the naloxone-precipitated jumping behavior in a dose dependent fashion (FIG. 3C).

Figure 3:
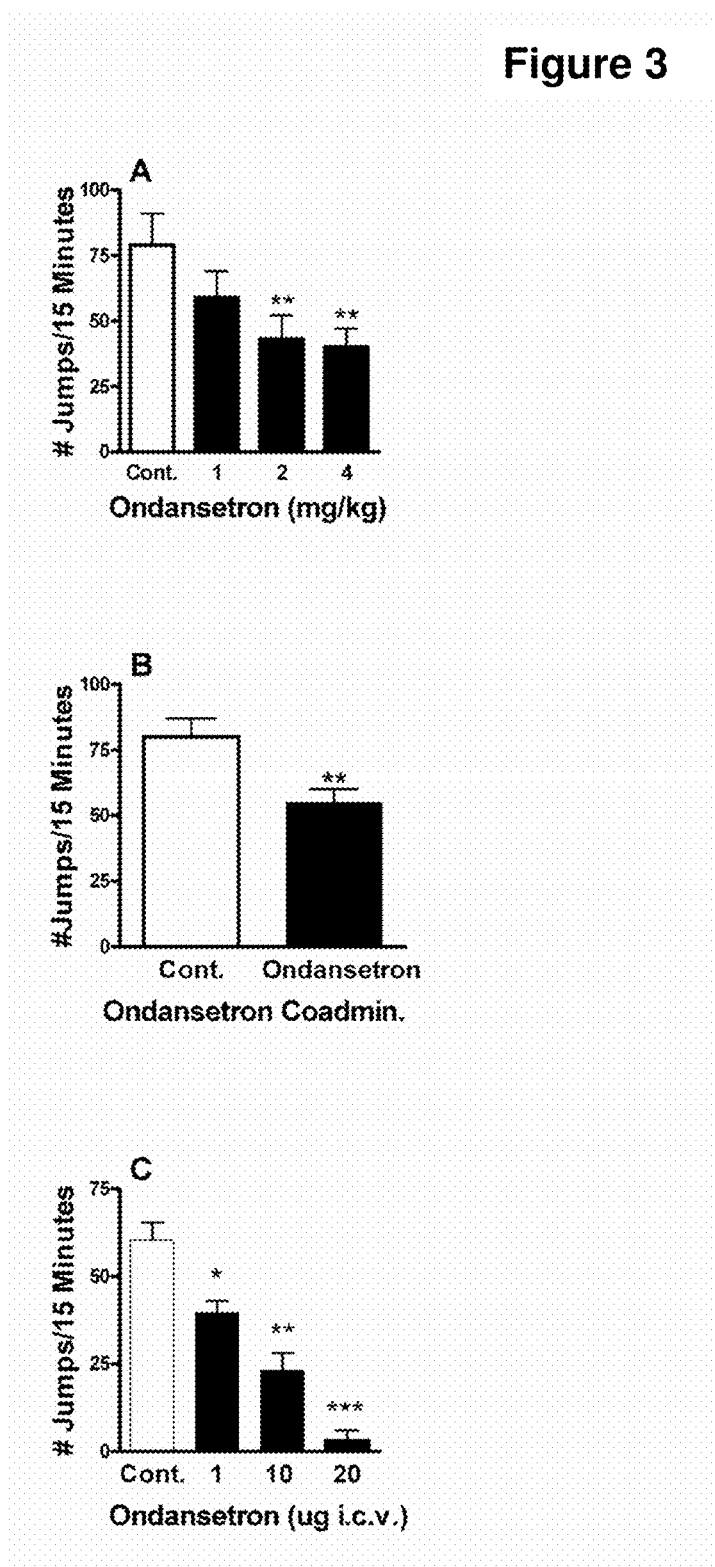
FIG. 3 illustrates administration of a selective 5-HT3 receptor antagonist (ondansetron) that decreases naloxone precipitated withdrawal behavior.

FIG. 3 demonstrates that administration of a selective 5-HT3 receptor antagonist (ondansetron) decreases naloxone precipitated withdrawal behavior. For FIG. 3A, mice (C57BL/6J) were treated with morphine over a four day period, and then were treated with saline or the indicated dose of ondansetron on the fifth day prior to assessment of naloxone-precipitated jumping behavior. Ondansetron treatment induced a statistically significant and dose-dependent reduction in jumping behavior. For FIG. 3B, mice (C57BL/6J) were treated with saline or ondansetron (1 mg/kg) at the time of each of the bi-daily morphine injections during the four day dependence building protocol. Eighteen hours after the final dose, naloxone-precipitated jumping behavior was assessed. For FIG. 3C, mice (C57BL/6J) were treated with saline or the indicated dose of ondansetron i.c.v. prior to assessment of naloxone-precipitated jumping behavior. Ondansetron treatment induced a statistically significant and dose-dependent reduction in jumping behavior. For all experiments 6-8 mice were used per group. Data represent mean values+/−SEM. *p<0.05, p<0.01, *p<0.001.

Experimental details for this Example can be found in Example 9.

Example 3

Ondansetron Treatment Reduces Morphine Dependence Related Hyperalgesia

Figure 4:
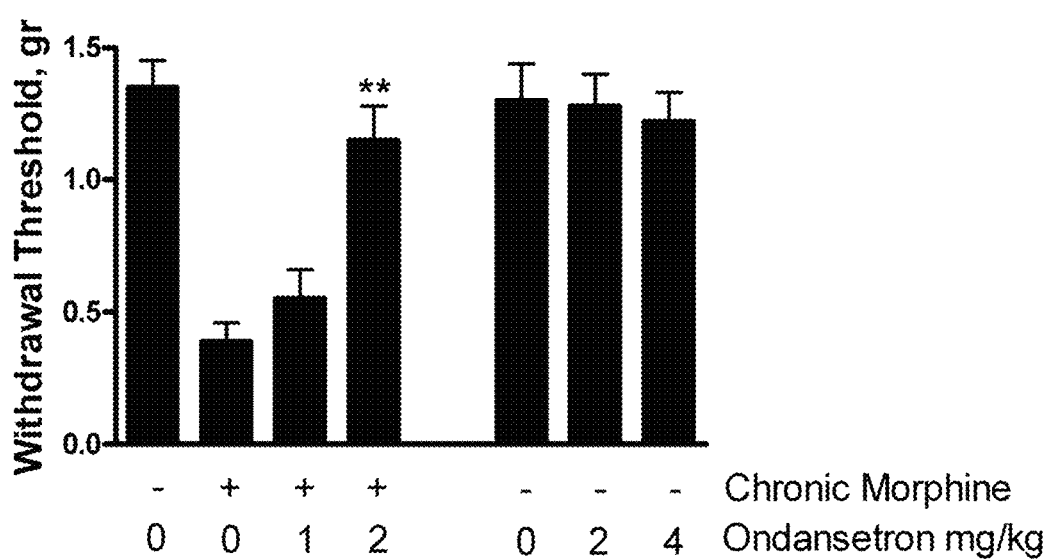
FIG. 4 illustrates that ondansetron treatment reduces morphine dependence related hyperalgesia.

The spontaneous hyperalgesia observed in humans and mice after chronic exposure to opioids, which is referred to as opioid-induced hyperalgesia (Angst, M. S. and J. D. Clark, *Anesthesiology*, 2006. 104(3): p. 570-587), is another measure of physical dependence (Chu, L. F et al., *J Pain*, 2006. 7(1): p. 43-48; Kayan, S., et al., *J Pharmacol Exp Ther*, 1971. 177(3): p. 509-513; Von Voigtlander, P. F. and R. A. Lewis, *J Pharmacol Methods*, 1983. 10(4): p. 277-282). In the present experiments, chronic morphine treatment caused hyperalgesia in C57BL/6J mice. Sensitization to a mechanical stimulus provides a robust degree of sensitization (Liang, D. Y., et al., *Anesthesiology*, 2006. 104(5): 1054-1062). Ondansetron administration had no effect on pain sensitivity in control mice that were not treated with morphine, but reversed the hyperalgesia that developed during morphine abstinence (FIG. 4). Taken together, these experiments demonstrate that a 5-HT3 receptor antagonist markedly reduced the severity of two distinct measures of physical dependence on morphine.

FIG. 4 demonstrates that ondansetron treatment reduces morphine dependence related hyperalgesia. The effect of the selective 5-HT3 antagonist ondansetron was evaluated in mice that were made dependent on morphine over a four day period. As a measure of physical dependence on morphine, mechanical nociceptive sensitization was measured 18 hours after administration of the last dose of morphine, the point of maximal nociceptive sensitization. Mice were treated with saline (control) or the indicated dose of ondansetron 30 minutes prior to threshold assessment. Ondansetron dose-dependently reversed the mechanical nociceptive sensitization caused by morphine withdrawal, but did not alter baseline nociceptive thresholds in control animals, even when doses of ondansetron higher than those effectively revering hyperalgesia were administered. Six mice per group were used in these experiments, and the data represent mean values+/− SEM. **p<0.01.

Experimental details for this Example can be found in Example 9.

Example 4

Ondansetron Blocks the Conditioned Place Preference Associated with Morphine Administration Because of the positive findings with respect to 5-HT3 blockade and reduction in signs of physical dependence, the testing was extended to a paradigm probing the reinforcing properties of opioid administration by using conditioned place preference (CPP). The group of mice that were administered morphine 5 mg/kg and placed in the conditioning chamber 25 min after injection had a mean difference between pre and post conditioning percentage of time spent in the compartment associated with drug of 21.29 percent (95%

Figure 5:
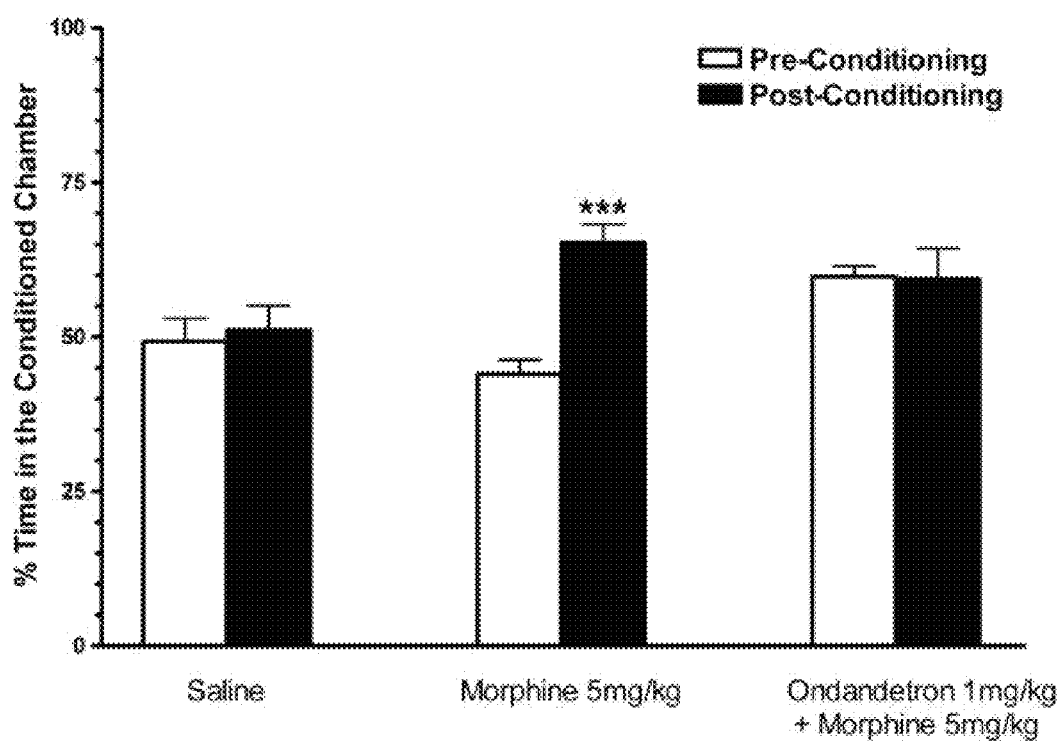
FIG. 5 illustrates that ondansetron blocks the conditioned place preference associated with morphine administration.

CI: 16.82 to 25.75; p<0.001). The group of mice that received ondansetron 1 mg/kg in addition to morphine 5 mg/kg displayed a mean difference of 0.40 percent (95% CI:—9.666 to 10.47; p=0.93) (FIG. 5). Thus ondansetron completely blocked the place preference associated with morphine administration.

FIG. 5 demonstrates that ondansetron blocks the conditioned place preference associated with morphine administration. In this figure the mean percent time spent in the assigned drug associated chamber in the conditioned place preference assessments before and after conditioning is displayed. Three groups of mice were used: Vehicle (n=15); Morphine 5 mg/kg (n=14); Ondansetron 1 mg/kg and morphine 5 mg/kg (n=10). ***p<0.001.

Experimental details for this Example can be found in Example 9.

Example 5

Morphine Treatment has a Differential and Brain Region-Specific Effect on HTR3A mRNA Expression Chronic morphine exposure reduces Htr3a mRNA expression within key brainstem nuclei. The intra-cerebroventricular injection experiments demonstrated that ondansetron modulated naloxone-induced jumping, by acting within the CNS. Furthermore, none of the SNPs within either Ht3a-associated haplotype block altered its predicted amino acid sequence. Many SNPs were located within '3 and '5 regulatory regions, suggesting that they may alter mRNA transcription or stability. Thus, differences in CNS Htr3a mRNA expression could be responsible for inter-strain differences in the severity of naloxone-precipitated withdrawal. To investigate this possibility, Htr3a mRNA expression in several brain regions in the presence or absence of chronic morphine treatment was evaluated. Measurements were made in strains with high (C57BL/6J) or low (129/SvlmJ) morphine dependence which possess different Htr3a haplotypes. Chronic morphine treatment induced strain and brain region specific changes in Htr3a expression (FIG. 6); the C57BL/6J strain exhibited a more drastic decrease in Htr3a mRNA in cortical and brainstem tissue, while the 129/SvlmJ strain exhibited a larger decrease in the cerebellum. An approximately equal change in the spinal cord Htr3a expression was observed in both strains.

Figure 6:
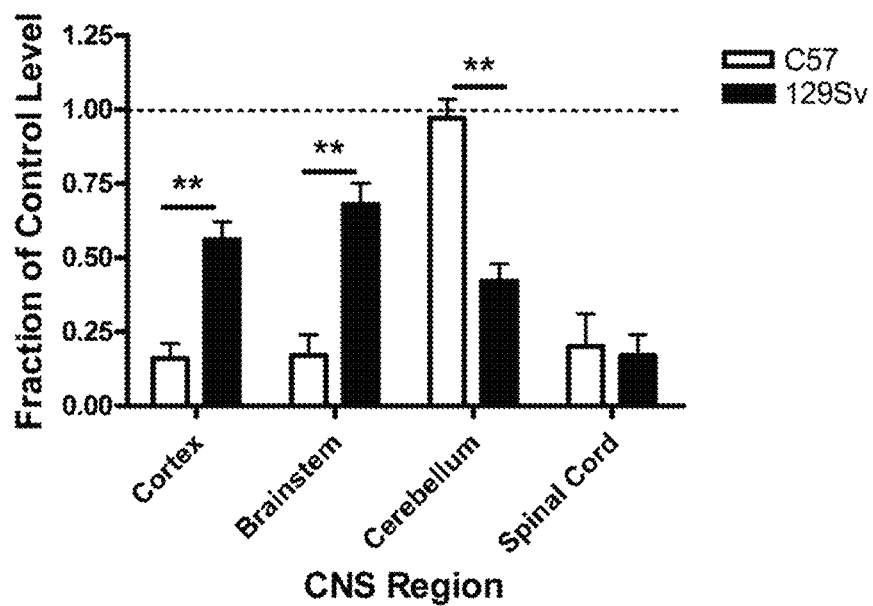
FIG. 6 illustrates that morphine treatment has a differential and brain region-specific effect on Htr3a mRNA expression.
Figure 6:
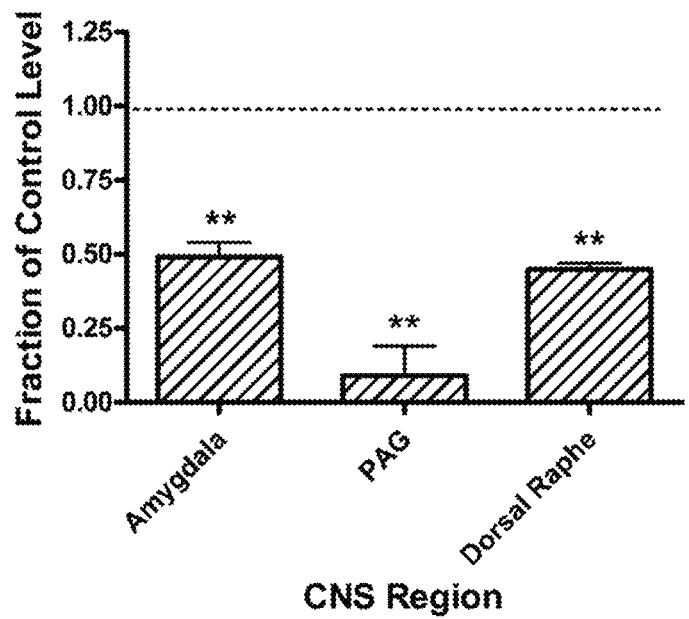

Whether chronic morphine exposure would alter Htr3a mRNA levels within specific brainstem nuclei that were previously associated with physical dependence on opioids was also investigated. The amygdala (Costall, B., et al., *Pharmacol Biochem Behav*, 1990. 36(1): p. 97-104; Gulati, A. and H. N. Bhargava, *Eur J Pharmacol*, 1989. 167(2): p. 185-192), dorsal raphe (Costall, B., et al., *Pharmacol Biochem Behav*, 1990. 36(1): p. 97-104; Tao, R., Z. Ma, and S. B. Auerbach, *J Pharmacol Exp Ther*, 1998. 286(1): p. 481-488) and periaqueductal gray (Ingram, S. L., et al., *J Neurosci*, 1998. 18(24): p. 10269-10276) are brainstem nuclei are known to modulate signs of opioid dependence and withdrawal. Tissue from these 3 brainstem regions was harvested from dependence-developing C57BL/6J mice by laser capture microdissection. Htr3a mRNA expression in all three of these brainstem nuclei was markedly reduced (2 to 5-fold) after chronic morphine treatment (FIG. 6). Consistent with the computational prediction, therefore, there are strain-specific differences in the effect of chronic morphine exposure on CNS Htr3a mRNA expression, and chronic morphine exposure reduced Htr3a mRNA in 3 brainstem nuclei associated with opioid dependence.

FIG. 6 demonstrates that morphine treatment has a differential and brain region-specific effect on Htr3a mRNA expression. For FIG. 6A, mice with a high (C57BL/6J) or low propensity (129Svlm/J) to develop morphine dependence were exposed to saline or morphine for four days. On the fifth day the mice were sacrificed, the indicated brain regions were dissected, and level of Htr3a mRNA expression was measured using real-time qPCR. Data represent mean values+/−SEM from duplicate measurements made on at least 6 mice per group. FIG. 6B demonstrates that morphine induces changes in Ht3a mRNA expression in selected brainstem nuclei. Mice (C57BL/6J) were treated with saline or morphine as above. The mice were then sacrificed, the indicated brainstem nuclei were isolated by laser capture microdissection, and Ht3a mRNA expression in the brainstem nuclei was analyzed. The Htr3a mRNA levels in morphine treated mice were normalized relative to those in saline treated animals. The data are displayed as the mean normalized value for tissues from n=6 mice per group+/−SEM. **p<0.01.

Experimental details for this Example can be found in Example 9.

Example 6

Regulation of CNS Expression for Several Genes by Morphine

The expression levels of several additional genes were measured as a specificity control in C57BL/6J and 129SvlmJ mice. There were no inter-strain differences after chronic morphine-treatment in the brain levels of expression of Kcnj6, C3ar1, C5ar1 or Htr3b mRNA between these 2 strains FIG. 7. Importantly, the Htr3b gene is located adjacent to Htr3a on chromosome 9, and encodes a protein that forms heteromultimeric 5-HT3 receptors, with biophysical properties that are distinct from Htr3a homomultimers (Brady, C. A., et al., *Neuropharmacology*, 2001. 41(2): p. 282-284).

Figure 7:
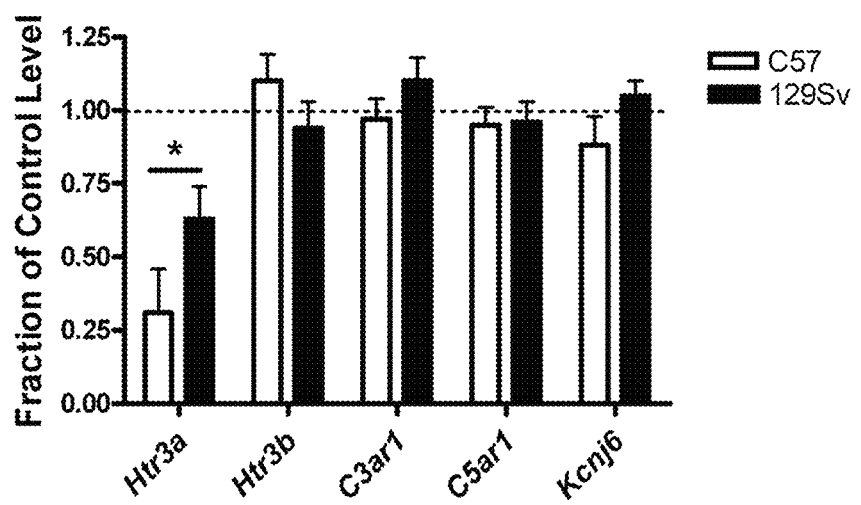
FIG. 7 illustrates the regulation of CNS expression for several genes by morphine.

FIG. 7 demonstrates the regulation of CNS expression for several genes by morphine. Brain tissue was harvested after four days of saline versus morphine treatment for both high (C57Bl/6J) and low (129/SvlmJ) dependence developing strains. In this survey of genes only expression of the Htr3a gene coding for the 5-HT3 serotonin receptor was opioid regulated (p<0.05). Importantly, expression of the adjacent Htr3b gene coding for an alternate form of the 5-HT3 receptor was not altered by morphine treatment. Five mice per group were used in these experiments, and the displayed data represent mean values+/−SEM. *p<0.05 (difference between strains).

Experimental details for this Example can be found in Example 9.

Example 7

Regulation of Brainstem 5-HT3 Protein Levels by Morphine

Chronic morphine exposure reduces 5-HT3 protein expression. Western blot analysis was conducted to determine if changes in 5-HT3 protein followed the observed changes in Htr3a mRNA. This analysis showed that protein preparations from the brainstems of C57BL/6J mice had statistically significant decreases in 5-HT3 content after morphine treatment while no such changes were observed in preparations made from 129/SvlmJ mice (FIG. 8).

Figure 8:
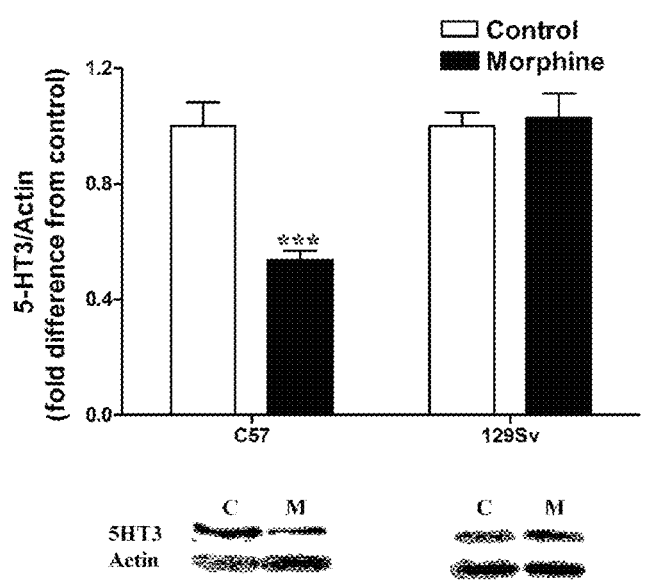
FIG. 8 illustrates the regulation of brainstem 5-HT3 protein levels by morphine.

FIG. 8 shows the regulation of brainstem 5-HT3 protein levels by morphine. Brain tissue was harvested after four days of saline versus morphine treatment for both high (C57B1/6J) and low (129/SvlmJ) dependence developing strains. Only in tissue from the C57B1/6J strain demonstrated morphine induced 5-HT3 changes. Five mice per group were used in these experiments, and the displayed data represent mean values+/−SEM. Average control mouse expression was set to 1. ***p<0.001 (difference between control and morphine treated groups).

Experimental details for this Example can be found in Example 9.

Example 8

Figure 9:
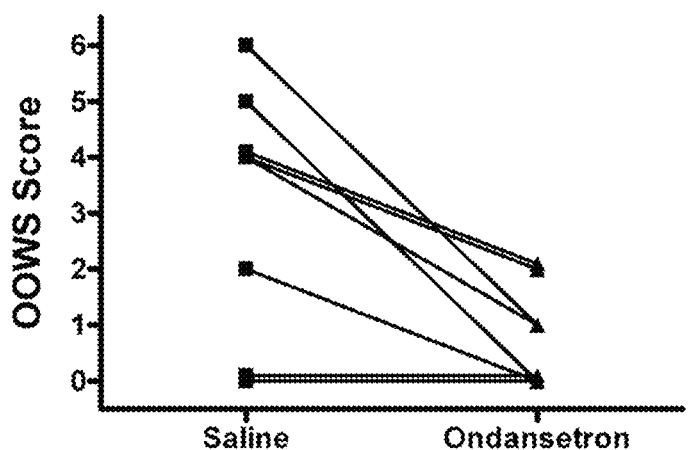
FIG. 9 illustrates the effect of ondansetron pretreatment on the acute, naloxone-precipitated withdrawal response in human subjects.
Figure 9:
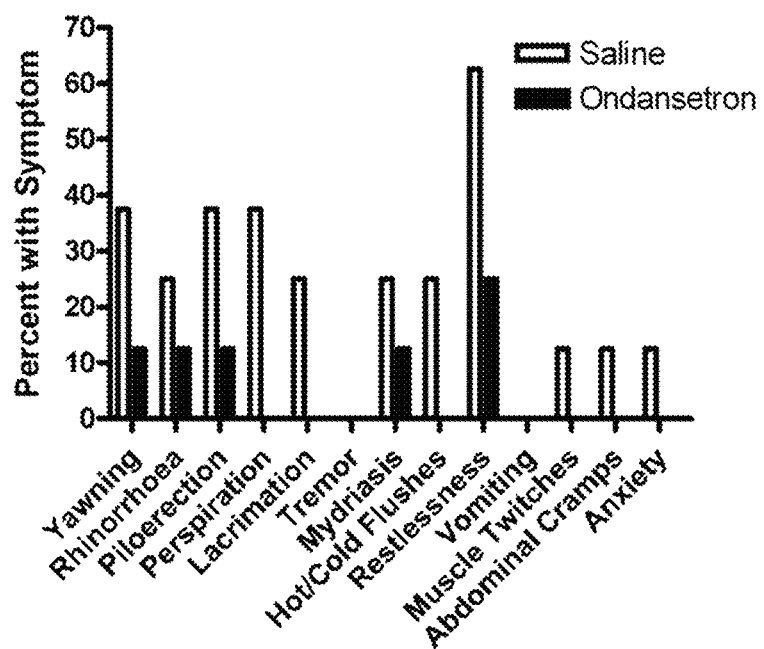

The Effect of Ondansetron Pretreatment on the Acute, Naloxone-Precipitated Withdrawal Response in Human Subjects Pre-treatment with ondansetron reduces signs of opioid withdrawal in humans. Based upon the murine results, the efficacy of the 5-HT3 receptor antagonist ondansetron was tested in human subjects using an experimental protocol for inducing opioid withdrawal (Compton, P., et al., *Pharmacol Biochem Behav*, 2004. 77(2): p. 263-268). Eight healthy male volunteers were pre-treated with placebo or ondansetron (8 mg) prior to intravenous administration of morphine and subsequent naloxone precipitated withdrawal. The effect of the pre-treatment drug was assessed using well-established objective (objective opioid withdrawal scale or OOWS, primary outcome) and subjective (subjective opioid withdrawal scale or SOWS) measures of opioid withdrawal (Handelsman, L., et al., *Am J Drug Alcohol Abuse*, 1987. 13(3): p. 293-308). Ondansetron pretreatment caused a substantial (76.4%±22.6) and statistically significant (p=0.0313) decrease in mean OOWS score (FIG. 9). Seven of the 8 subjects developed objective signs of opioid withdrawal, and ondansetron pre-treatment reduced these signs in all seven affected individuals. The OOWS score is a composite measure of thirteen physically observable signs. The volunteers manifested 12 of the 13 measured signs, and ondansetron pre-treatment decreased all 12 of these individual signs indicating abroad-spectrum effect (FIG. 9). In contrast, there was only a very small mean decrease in the subjective symptoms (SOWS score) that did not reach statistical significance (4.1%±62.5, p>0.05, FIG. 10).

FIG. 9 shows the effect of ondansetron pretreatment on the acute, naloxone-precipitated withdrawal response in human subjects. Ondansetron 8 mg IV or placebo (normal saline) IV was administered 30 minutes prior to morphine (10 mg/70 kg) IV administration in 8 subjects. Naloxone-precipitated (10 mg/70 kg) withdrawal was then induced 120 minutes after morphine administration. In FIG. 9A, the composite OOWS scores for each subject after naloxone-precipitated opioid withdrawal after saline or ondansetron pretreatment are displayed. A p-value=0.0313 was calculated based on signed rank test of the difference in OOWS score after pre-treatment with ondansetron and placebo. In FIG. 9B, the OOWS sub-category responses to ondansetron pretreatment are displayed. The OOWS scale is composed of thirteen physically observable signs, which are rated as present (1) or absent (0) during the observation period. The percent of the volunteers who experienced each indicated naloxone-precipitated withdrawal sign after ondansetron or placebo pre-treatment is shown.

Figure 10:
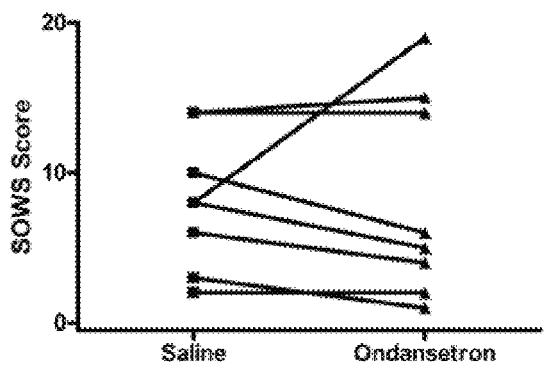
FIG. 10 illustrates the effect of ondansetron pretreatment on the acute, naloxone-precipitated Subjective Opiate Withdrawal Scale (SOWS) response in human subjects.
Figure 10:
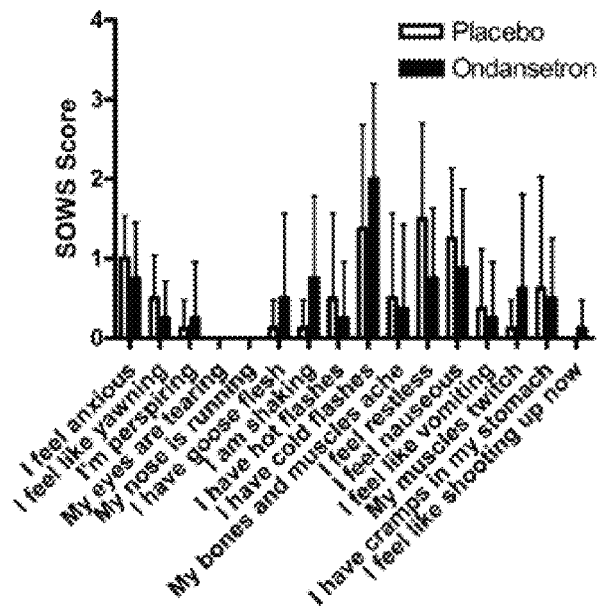

FIG. 10 shows the effect of ondansetron pretreatment on the acute, naloxone-precipitated Subjective Opiate Withdrawal Scale (SOWS) response in human subjects. Ondansetron 8 mg IV or placebo (normal saline) IV was administered 30 minutes prior to morphine (10 mg/70 kg) IV administration in eight subjects. Naloxone-precipitated (10 mg/70 kg) opioid withdrawal was then induced 120 minutes after morphine administration. In FIG. 10A, the composite SOWS scores for each subject after naloxone-precipitated opioid withdrawal for subjects receiving saline or ondansetron pretreatment are displayed. A p-value=0.5625 was calculated based on signed rank test of the difference in SOWS score after pre-treatment with ondansetron and placebo. In FIG. 10B, the SOWS subcategory responses to ondansetron pretreatment in humans are displayed. The SOWS score is composed of sixteen subjective symptoms rated on a scale of 0 to 4 (0=not at all, 1=a little, 2=moderately, 3=quite a bit, 4=extremely) based on what subjects were experiencing at the time of testing. The mean score for volunteers who experienced each indicated naloxone-precipitated withdrawal symptom after ondansetron or placebo pretreatment is shown.

Experimental details for this Example can be found in Example 9.

Example 9

Experimental Details for Examples 1-8

Animals

All animal experiments were conducted using protocols approved by an Institutional Animal Care and Use Committee. Protocols complied with the Guide for the Care and Use of Laboratory Animals available through the National Academy of Sciences.

Male mice from the inbred mouse strains (129/SvlmJ, A/HeJ, A/J, AKR/J, B10.D2-H2/oSNJ, BALB/cByJ, BALB/cJ, BUB/BnJ, C3H/HeJ, C57BL/6J, DBA/2J, FVB/NJ, LP/J, LG/J, MRL/MpJ, NZB/BinJ, NZW/LaCJ, SM/J) were obtained from Jackson Labs (Bar Harbor, Me.) at 7-8 weeks of age, and housed for 7-10 days in an animal care facility for acclimation prior to use in experiments. Mice were kept under pathogen-free conditions and were provided food and water ad libitum with a 12:12 h light:dark cycle.

Behavioral Assays

Morphine treatment—After baseline nociceptive testing, morphine (Sigma Chemical, St. Louis, Mo.) was administered to mice subcutaneously (s.c.) 10 mg/kg twice per day on day 1, 20 mg/kg on days 2-3 and 40 mg/kg twice per day on day 4 in 50-100 volumes of 0.9% NaCl similar to previous protocols for generating opioid-induced hyperalgesia (OTH), tolerance and dependence (Liang, D. Y., et al. *Pain*, 2006. 121(3): p. 232-240; Liang, D. Y., et al., *Pharmacogenet Genomics*, 2006. 16(11): p. 825-835. Liang, D. Y., et al., *Anesthesiology*, 2006. 104(5): p. 1054-1062).

Precipitated withdrawal—For dependence determinations, mice were assessed 18 hours after the final dose of morphine when spontaneous dependence-related hyperalgesia was maximal (Lin, R. J., et al., *Oncogene*, 2001. 20(49): p. 7204-7215). Naloxone (Sigma Chemical) 10 mg/kg was injected s.c. in 50 µl NaCl as described previously (Kest, B., et al., *Pharmacol Biochem Behav*, 2002. 73(4): p. 821-828; Liang, D. Y., et al., *Pain*, 2006. 121(3): p. 232-240). After naloxone administration, mice were placed in clear plastic cylinders (10 cm in diameter and 40 cm in height, and the number of jumps during the following 15 minutes were counted. Naloxone precipitated jumping behavior is a robust response reflecting physical dependence on opioids observed across strains of inbred mice (Kest, B., et al., *Neuroscience* 2002. 115(2): 463-469).

In some experiments the selective 5-HT3 antagonist ondansetron (Sigma) was administered. For systemic administration, ondansetron was injected subcutaneously in 100 volumes of 0.9% NaCl to some groups of mice. The drug was either given at a dose of 1 mg/kg along with each dose of morphine during the chronic dosing paradigm, or given once over a range of doses 30 minutes prior to dependence or nociceptive testing. For intracerebroventricular (i.c.v.) administration, mice were briefly anesthetized with inhaled isoflurane. A 30 gauge ½ inch needle was used to pierce the skull and enter the ventricles using an approach described previously (Pedigo, N. W. et al. *J Pharmacol Exp Ther*, 1975. 193(3): p. 845-852). Once inserted, 5 µl of injectate was slowly administered using a microsyringe, and the animals were used within 20 minutes after the injection.

Opioid dependence related hyperalgesia—Mechanical allodynia was assayed using nylon von Frey filaments according to the "up-down" algorithm described by Chaplan et al. (Chaplan, S. R., et al., *J Neurosci Methods*, 1994. 53(1): p. 55-63) as previously described (Liang, D. Y., et al., *Anesthesiology*, 2006. 104(5): p. 1054-1062; Li, X et al., *Brain Res Mol Brain Res*, 2001. 86(1-2): p. 56-62). In these experiments, mice were placed on wire mesh platforms in clear cylindrical plastic cylinders. After 15 minutes of acclimation, fibers of sequentially increasing stiffness were applied to the plantar surface of one hind paw, pressed upward to cause a slight bend in the fiber and left in place 5 sec. Withdrawal of the hind paw from the fiber was scored as a response. When no response was obtained the next stiffest fiber in the series was applied to the same paw; if a response was obtained a less stiff fiber was applied. Testing proceeded in this manner until 4 fibers had been applied after the first one causing a withdrawal response allowing the estimation of the mechanical withdrawal threshold (Poree, L. R., et al., *Anesth Analg*, 1998. 87(4): p. 941-948). This data fitting algorithm allowed the use of parametric statistics for analysis. This assay is sufficiently sensitive to detect mechanical thresholds as low as 0.02 g (Liang, D. Y., et al., *Anesthesiology*, 2006. 104(5): p. 1054-1062).

Conditioned place preference (CPP)—To assess the dependence liability of morphine and subsequent effects of ondansetron on such dependence, a counter balanced conditioned place preference (CPP) paradigm was employed (Bardo, M. T., et al. *Neurosci Biobehav Rev* 1995. 19(1): 39-51; Reid, L. D., et al. *Pharmacol Biochem Behav* 1989. 33(4): 765-775). The CPP experiments were performed using Place Preference System (MED Associates Inc., St. Albans, Vt.), which consists of three compartments; two outer compartments for active association and a middle neutral compartment. One association compartment is constructed of white opaque plastic walls with a floor made of metal rods while the other compartment is made of black opaque plastic walls with a metal mesh floor. The smaller middle neutral compartment is made of gray opaque plastic walls and floor. The smaller middle neutral compartment is made of gray opaque plastic walls and floor. Experiments were conducted in a dimly lit room with homogenous lighting (~20 lux). The place preference apparatus is equipped with motion photosensors with data recorded via a computer running MED PC software (MED Associates Inc, Vt.). C57B1/6J mice (8 to 12 weeks old) were used in all experiments, which were carried out during the second half of the light phase between 13:00-18:00 hr. On Day 0, the mice were acclimated to the test room and the time spent in each compartment was recorded (pre-conditioning report). Any mouse that spent more than 75% of the time in either of the association compartments was excluded. On the following day each mouse was randomized to a control or drug group and assigned to either the white or black association compartments in a counter-balanced fashion (n=10-15 per group). On Days 1, 3, and 5 the drug group received intraperitoneal (i.p.) injections of the drug(s): vehicle (0.9% saline), morphine 5 mg/kg or ondansetron 1 mg/kg plus morphine 5 mg/kg (separate injections). Twenty-five minutes after injection(s), each mouse was placed into its assigned association compartment for 25 min without access to the other compartments. On Days 2, 4 and 6, the mice received saline injections and were placed in the alternative compartment after 25 min. On Day 7, mice were placed in the middle neutral compartment of the place preference apparatus with full access to the other two compartments and assessed for the length of time spent in each compartment (post-conditioning report). The percentage of time spent in each association compartment was calculated relative to the total time spent in both association compartments.

Computational Haplotype-Based Genetic Mapping

Haplotype-based computational genetic analysis of the phenotypic data was performed as previously described (Wang, J., et al., *Trends Genet*, 2005. 21(9): p. 526-532; Liang, D. Y., et al., *Anesthesiology*, 2006. 104(5): p. 1054-1062; Guo, Y., et al., *Nat Biotechnol*, 2006. 24(5): p. 531-536; Liang, D. Y., et al., *Behav Brain Res*, 2007. 181(1): p. 118-126). This technique has been used recently to identify genes associated with a number of different murine phenotypic traits including opioid narcotic drug responses (Liang, D. Y., et al., *Pain*, 2006. 121(3): p. 232-240; Liang, D. Y., et al., *Pharmacogenet Genomics*, 2006. 16(11): p. 825-835; Liang, D. Y., et al., *Anesthesiology*, 2006. 104(5): p. 1054-1062; Smith, S. B., et al., *Pharmacogenet Genomics*, 2008. 18(3): p. 231-241). In brief, allelic data from multiple inbred strains were analyzed and a haplotype block map of the mouse genome was constructed. Only a limited number of haplotypes—typically 2, 3 or 4—are present within a haplotype block. This analysis identifies haplotype blocks in which the haplotypic strain grouping within a block correlates with the distribution of phenotypic data among the inbred strains analyzed. To do this, a p-value that assesses the likelihood that genetic variation within each block could underlie the observed distribution of phenotypes among the inbred strains is calculated as described using ANOVA (Wang, J., et al., *Trends Genet*, 2005. 21(9): p. 526-532; Liao, G., et al., *Science*, 2004. 306(5696): p. 690-695). The phenotypic data was evaluated using the average value for each strain, obtained by assessing 8 mice per strain. The haplotype blocks are then ranked based upon the calculated p-value. When this computational analysis was performed, the haplotype map had 5,694 haplotype blocks generated from 215,155 single nucleotide polymorphisms (SNPs) characterized across 19 inbred strains covering 2,609 genes. From this analysis, the candidate haplotype blocks empirically selected for further analysis had the best p-values.

Gene Expression Analysis

Mice were sacrificed at specific time points by $CO_2$ asphyxiation. Whole brains were dissected en block from the skull, and spinal cords were harvested by extrusion. Using low power binocular magnification, tissues were dissected on a chilled surface. Brain tissue was separated into cortex, cerebellum and brainstem. Dissected tissue was then quick frozen in liquid nitrogen and stored at −80° C. until use. Total RNA was isolated using the RNeasy Mini Kit (Qiagen, Valencia, Calif.) according to the manufacturer's instructions, its purity and concentration were determined spectrophotometrically as described previously for brain and spinal cord samples (Li, X., et al., *J Neurosci Res*, 2004. 78(4): p. 533-541). cDNA was synthesized from total RNA using random hexamer priming and a First Strand cDNA Synthesis Kit (Invitrogen, Carlsbad, Calif.). Briefly, 1 µg of total RNA was mixed with 4 µl of 10×RT buffer, 8 µl of 25 mM $MgCl_2$, 4 µl 0.1M DTT, 1 µl RNasin, 2 µl SSII (50 u/µl), 5 µl hexomers and RNase-free water to 40 µl. Incubation was then carried out at 42° C. for 60 minutes followed by heat inactivation at 70° C. Finally 1 µl RNase H was added to each reaction and incubated at 37° C. for 20 minutes to degrade the RNA. For real-time quantitative PCR, reactions were conducted in a volume of 4 µl using the Sybr Green I master kit (PE applied Biosystems, Foster City, Calif.). Briefly, 2 µl of a mixture of 2× sybr green and primers was loaded with 2 µl diluted cDNA template in each well. Following this, 8 µl mineral oil was loaded in each well to prevent loss of solution. Using an ABI prism 7900HT system, PCR was carried out using the parameters 52° C., 5 min→95, 10 min then [95° C., 30 s→60° C., 60 s] for 40 cycles. Samples were analyzed in triplicate. Melting curves were performed to document single product formation, and agarose electrophoresis confirmed appropriate product size. 18 s RNA was used as an internal control. The 18 s primers were purchased from Ambion (Austin, Tex.). The expression of Htr3a in morphine treated versus control samples was analyzed using the $\Delta\Delta C_t$ method (Liang, D., et al., *Neuroscience*, 2003. 121(4): p. 999-1005).

A previously described technique for Laser Capture Microdissection (LCM) of CNS tissue was used (Li, X., et al., *J Neurosci Res*, 2004. 78(4): p. 533-541). Mice underwent intracardiac perfusion with 10 cc ice cold 0.9% NaCl after $CO_2$ asphyxiation followed by brain harvest. Brainstems were rapidly dissected, embedded in OCT medium, and stored at −80° C. until sectioning. Later, 15 µM sections were cut using a cryostat, placed on slides and rapidly dehydrated through ethanol and xylene. Each slide contained about 6 sections. The slides were then brought directly to the PixCell LCM instrument (Arcturus, Mountain View, Calif.), with a 15 µm laser spot diameter, power of 40 mW and 500 µsec pulse duration to transfer tissue to the CapSure matrix (Arcturus). Each cap was used until 80-90% of the surface contained transferred tissue. Tissue was harvested from the amygdala, dorsal raphe and periquadctal gray nuclei using standard brain atlases to guide the process. The RNA was extracted using the PicoPure (Arcturus) RNA spin column purification kit according to manufacturer's directions followed by mRNA amplification. Amplification of laser captured RNA clarifies rather than distorts differences between samples (Feldman, A. L., et al., *Biotechniques*, 2002. 33(4): p. 906-12, 914). This process was performed using the RiboAmp RNA amplification kit (Arcturus) according to the manufacturer's directions for a single round of amplification, and the amount of material was quantified by absorbance spectrophotometry and then subjected to reverse transcription using random hexomer primers as described above. Amplified mRNA was then used for real time PCR based quantification as described.

Western blotting for 5-HT3 receptor protein was performed as described (Liang, D. Y. and J. D. Clark, *Neurosci Lett*, 2004. 365(1): p. 73-77). Briefly, tissues from specific CNS regions were homogenized in protease containing buffer and run on separated on acrylamide gels. After transfer, membranes were probed using rabbit polyclonal anti-5-HT3 antibody (abcam, Cambridge, Mass.) at 1:500 dilution. Membranes were then stripped and re-probed for actin abundance thus allowing normalization.

Human Subjects, Study Design and Procedures

Eight healthy male volunteers underwent an acute precipitated narcotic drug withdrawal protocol as previously described (Compton, P., et al., *Pharmacol Biochem Behav*, 2004. 77(2): p. 263-268) with or without ondansetron pretreatment using a randomized double-blinded placebo-controlled crossover study design on two separate occasions. Test sessions for each individual subject were separated by at least seven days. Female volunteers were excluded from the study due to modulation of opioid response by menstruation cycles (Hoehe, M., *Psychoneuroendocrinology*, 1988. 13(4): p. 339-344). The human experimental protocol was approved by the Institutional Review Board (Stanford University). Each volunteer provided written informed consent prior to study enrollment, and the study was registered in the clinicaltrials.gov database (identifier NCT00661674).

All study sessions were conducted by a blinded research assistant (ND) and supervised by an un-blinded physician (LC) who administered the study medication and monitored heart rate, blood pressure and arterial oxygenation throughout the study. The subjective opioid withdrawal scale (SOWS) and objective opioid withdrawal scale (OOWS) were completed after establishing intravenous access and before administration of study medications, as originally described by Handelsman et al (Handelsman, L., et al., *Am J Drug Alcohol Abuse*, 1987. 13(3): p. 293-308). All OOWS measurements were obtained by the same blinded research assistant (ND). Ondansetron (Bedford Laboratories, Bedford, Ohio) 8 mg or placebo (0.9% saline solution, Hospira Inc., Lake Forest, Ill.) was administered in a double-blinded fashion as an IV bolus. Thirty minutes later, Morphine (Baxter Healthcare Corp., Deerfield, Ill.) 10 mg/70 kg was administered over 10 minutes. Patients remained in the lab under observation for 105 minutes and were offered music or video entertainment and caffeine-free meals or snacks ad lib during this period of time. After 105 minutes, the patient's vital signs and OOWS and SOWS were reassessed. 120 minutes after IV morphine administration, 10 mg/70 kg naloxone (Hospira Inc., Lake Forest, Ill.) was administered to the subject as an intravenous bolus. Vital signs, SOWS and OOWS were administered five minutes and fifteen minutes after the naloxone administration.

Statistical Analysis

All data are displayed as the means+/−SEM unless otherwise noted. Animal behavioral data was analyzed using one or two-way ANOVA with post-hoc Tukey testing or, for conditioned place preference data with t-testing. The outcome measures of interest between the placebo- and ondansetron-treated groups were compared using paired t test and the Wilcoxon Signed Rank test where appropriate. Normal distribution was determined using QQ plots and the Kolmogorov-Smirnov test. Analyses were performed with SAS 9.1 statistical package (Cary, Ill.) with p<0.05 considered statistically significant.

Example 10

Figure 11:
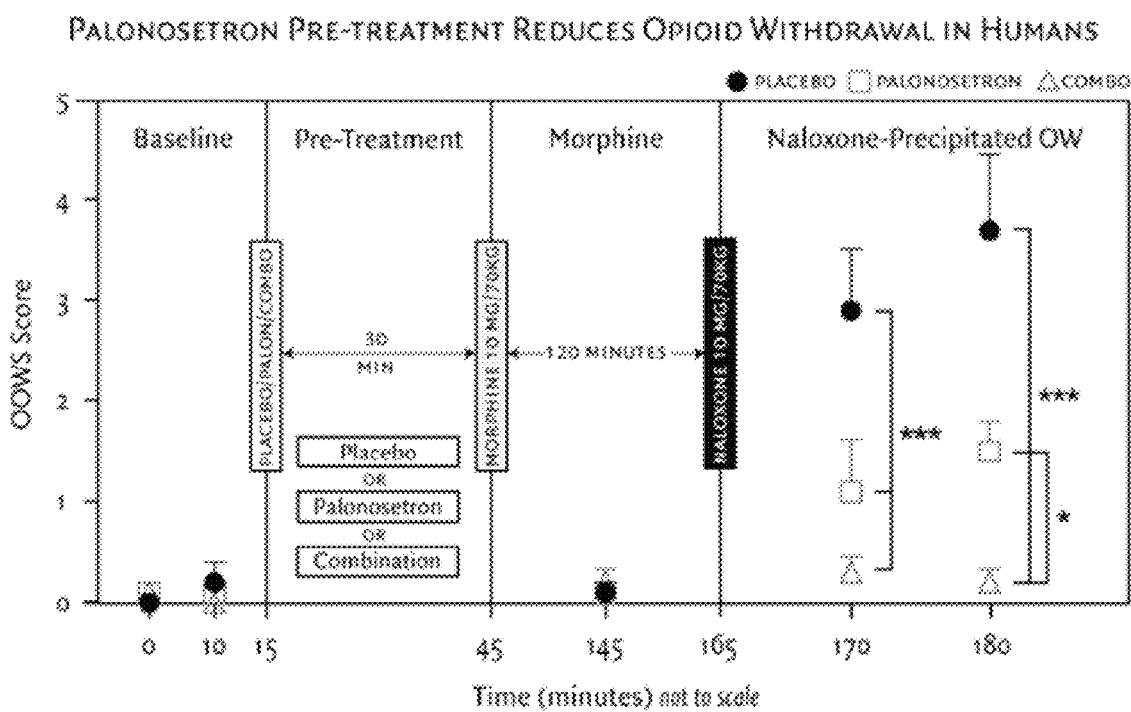
FIG. 11 illustrates the effect of combining a 5-HT3 antagonist with an antihistamine is treatment of withdrawal symptoms.

Combination of 5-HT3 Antagonist and Antihistamine in Treating Narcotic Withdrawal Symptoms In these studies, palonosetron (a 5-HT3 antagonist) was administered alone, or in combination with a clinically available antihistamine (hydroxyzine) to human volunteers. As shown in FIG. 11, treatment with palonosetron (0.75 mg IV) alone reduced the naloxone-induced withdrawal symptoms in 12 male volunteers relative to placebo control (P<0.01).

However, the combination of the 5-HT3 antagonist and the antihistamine (hydroxyzine 100 mg PO (taken by mouth)), both administered at average clinical doses, caused a very profound reduction in the objective withdrawal signs of withdrawal. Of note, the reduction achieved by the combination therapy was significantly ($P<0.05$) better than that caused by administration of palonosetron alone. These data indicate that a synergistic combination of medications can have increased efficacy in alleviating narcotic drug withdrawal symptoms in human volunteers.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating physical dependence and/or withdrawal symptoms associated with narcotic use, comprising administering to a human subject in need thereof a pharmaceutical composition consisting essentially of
   (1) a narcotic compound selected from the group consisting of morphine, hydrocodone, oxycodone, hydromorphone, and oxymorphone, buprenorphine and a combination of buprenorphine and naloxone, wherein said composition is administered at a dose of between 2 and 25 mg/70 kg of subject; and
   (2) a 5-HT3 receptor antagonist in a dose effective to reduce physical dependence and/or withdrawal symptoms associated with said narcotic use, wherein
   the narcotic compound and the 5-HT3 receptor antagonist are co-administered.

2. The method of claim 1 further comprising the step of administering to said human subject an antiemetic antihistamine.

* * * * *

UNITED STATES PATENT AND TRADEMARK OFFICE
CERTIFICATE OF CORRECTION

PATENT NO. : 9,226,918 B2  
APPLICATION NO. : 12/631628  
DATED : January 5, 2016  
INVENTOR(S) : Peltz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,477 days.

Signed and Sealed this
Sixteenth Day of August, 2016

Michelle K. Lee
*Director of the United States Patent and Trademark Office*